US008862656B2

(12) United States Patent
Olchanski et al.

(10) Patent No.: US 8,862,656 B2
(45) Date of Patent: Oct. 14, 2014

(54) PERFORMANCE OUTCOMES BENCHMARKING

(75) Inventors: Vladislav Olchanski, Richmond, VA (US); Viktor E. Bovbjerg, Richmond, VA (US); Stephen E. Zimberg, Weston, FL (US); Louis F. Rossiter, Richmond, VA (US); Vadim Polyakov, Richmond, VA (US); Jennifer S. Green, Lynchburg, VA (US)

(73) Assignee: Chironet, LLC, Richmond, VA (US)

( * ) Notice: Subject to any disclaimer, the term of this patent is extended or adjusted under 35 U.S.C. 154(b) by 1101 days.

(21) Appl. No.: 09/996,475

(22) Filed: Nov. 20, 2001

(65) Prior Publication Data

US 2003/0158749 A1 Aug. 21, 2003

Related U.S. Application Data

(60) Provisional application No. 60/252,129, filed on Nov. 21, 2000.

(51) Int. Cl.
*G06F 15/16* (2006.01)
*G06Q 10/10* (2012.01)
*G06Q 10/06* (2012.01)
*G06Q 50/22* (2012.01)

(52) U.S. Cl.
CPC .............. *G06Q 10/06* (2013.01); *G06Q 10/10* (2013.01); *G06Q 50/22* (2013.01)
USPC ........................................................ 709/203

(58) Field of Classification Search
CPC ........................ Y10S 128/923; H04L 12/6418

USPC .................. 709/206, 218, 205, 224; 315/331; 705/2, 3

See application file for complete search history.

(56) References Cited

U.S. PATENT DOCUMENTS

| | | | | |
|---|---|---|---|---|
| 3,675,640 A | * | 7/1972 | Gatts | 600/484 |
| 4,852,570 A | * | 8/1989 | Levine | 600/301 |
| 5,299,119 A | * | 3/1994 | Kraf et al. | 600/509 |
| 5,562,596 A | * | 10/1996 | Pincus et al. | 600/17 |
| 5,835,384 A | * | 11/1998 | Lin | 702/84 |
| 6,101,478 A | * | 8/2000 | Brown | 705/2 |
| 6,223,164 B1 | * | 4/2001 | Seare et al. | 705/2 |
| 6,424,996 B1 | * | 7/2002 | Killcommons et al. | 709/206 |
| 6,436,058 B1 | * | 8/2002 | Krahner et al. | 600/587 |
| 6,650,932 B1 | * | 11/2003 | Menzie et al. | 600/513 |
| 2002/0107769 A1 | * | 8/2002 | Dashefsky et al. | 705/35 |
| 2003/0013951 A1 | * | 1/2003 | Stefanescu et al. | 600/407 |
| 2004/0044274 A1 | * | 3/2004 | Bardy | 600/300 |
| 2004/0249675 A1 | * | 12/2004 | Stark et al. | 705/2 |

OTHER PUBLICATIONS

V. E. Bovbjerg et al., The Joint Commission—Journal on Quality Improvement, vol. 26, No. 8, 2000, "Internet-Based Monitoring and Benchmarking in Ambulatory Surgery Centers", pp. 450-465.

* cited by examiner

*Primary Examiner* — Karen Tang
(74) *Attorney, Agent, or Firm* — Wilmer Cutler Pickering Hale and Dorr LLP

(57) ABSTRACT

A technique for benchmarking performance outcomes is disclosed. In one embodiment, the technique is realized by creating and managing feedback reports for a benchmarking process. More particularly the technique includes acquiring primary data at the source, compiling the data in an analytically meaningful manner for benchmarking, preparing web-based reports and maintaining and managing cumulative historical data and reports.

29 Claims, 23 Drawing Sheets

FIGURE 3

Uploading Medical Records and Patient Interview Information

1. Have you connected to the internet?

Click below if yes.

If no, exit and connect to your internet provider.

[Yes, next step]   [No, exit]

2. Click on button below to ensure stable connection.

[Click to check]   You are connected to the Internet.

3. Click on button below to upload information.

[Upload Information]   Upload Successful

4. Move data from daily files to stock.

[Click to move files]   Files have been moved

5. Process complete, close this application.

[Click to Exit]

FIGURE 4

SAMPLE CENTER

EXECUTIVE BENCHMARK TABLE: INDICATOR STATUS AND TRENDS
Quarter 1, 1999 to Quarter 4, 1998
Table was created on 09/16/1999

| | Arthroscopy, Knee | Carpal Tunnel | Cataract Removal | Hernia Repair | Laparoscopy, Gyne |
|---|---|---|---|---|---|
| Perioperative Complications (ind1) | ⊙↘ | ●↘ | ⊙⇔ | ⊙- | ⊙↗ |
| Delayed in Discharge (ind2) | ●↗ | ●↗ | ●↘ | ⊙ | ○↘ |
| Returns to Surgery (ind3) | ⊙⇔ | ⊙⇔ | ⊙⇔ | ⊙ | ⊙⇔ |
| Admits to Hospital (ind4) | ⊙⇔ | ⊙⇔ | ⊙⇔ | ⊙ | ⊙⇔ |
| Pain Episodes Not Relieved (ind5) | ⊙⇔ | ⊙⇔ | ⊙↗ | ⊙ | ⊙⇔ |
| Care Not Needed After Discharge (IND6) | ⊙⇔ | ⊙↘ | ⊙⇔ | ⊙ | ⊙↘ |
| Pain Controlled After Discharge (IND7) | ○↗ | ⊙↗ | ⊙↗ | ⊙ | ⊙↗ |
| Satisfied Patients (IND8) | ⊙↗ | ⊙↗ | ⊙↗ | ⊙ | ⊙↗ |
| Effective Discharge Instructions (IND9) | ⊙⇔ | ⊙⇔ | ⊙⇔ | ⊙ | ⊙⇔ |
| Patients Prepared for Self-Care (IND10) | ⊙⇔ | ⊙⇔ | ⊙⇔ | ⊙ | ⊙⇔ |

Comparison with all centers (where you are now)
- ○ - Better than average
- ⊙ - Average
- ● - Worse than average Comparison of current results with those for the previous period (where you are going)
- ↗ - Improving
- ⇔ - No change
- ↘ - Worsening Return to Previous Screen

FIGURE 5

```
[_REPORT_SYSTEM] ──────────── 1000
|
+---[Data] ──────────────── 1100
|   |  Soix.mdb
|   +---[archive]
|   |     yyyymmdd.zip
|   \---[backup]
|       \---[yyyymmdd]
|           +---[AAA]
|           |       MEDUP.DBF
|           |       PATUP.DBF
|           \---[XYZ]
|                   MEDUP.DBF
|                   PATUP.DBF
+---[INI] ──────────────── 1200
|        Info.txt
|        report.ini
+---[Log] ──────────────── 1300
|        Executive_Table.log
|        Comparison_table.log
|        DataTable.log
|        Data_calculator.log
|        Executive_Table_Paper_Reports.log
|        GrabFile.log
|        ProcDistrib.log
|        report.log
+---[LST] ──────────────── 1400
|   |    Comparison_table.lst
|   |    Corporate_Members.lst
|   |    DataTableItems.lst
|   |    Executive_Table.lst
|   |    Indicators.lst
|   |    LogMessages.lst
|   |    ProcConv.lst
|   |    ProcDistrib.lst
|   |    Sites.lst
|   |    Stage1.lst
|   |    Stage2.lst
|   |
|   \---[Templates] ──────── 1500
|          Sample-Sites.lst
|          Full_List_Sites.lst
+---[Programs] ──────────── 1600
|   +---[Paper_Reports]
|   |       Executive_Table_Paper_Reports.exe
|   |       Comparison_table.exe
|   \---[Web_Reports]
|           APPENDER.mdb
|           Chart_Generator.exe
|           Executive_Table.exe
|           DataTable_Creator.exe
|           Data_Calculator.exe
|           ProcDistrib_Creator.exe
\---[Template] ──────────── 1700
    |    Age_Distribution2.html
    |    Anest.html
    |    Anest2.html
    |    ind.html
    |    ind2.html
    |    index-Old.html
    |    loopback.html
    |    main-Old.html
    |    main-Template.html
    |    main.html
    |    Payor.html
    |    Payor2.html
    |    RecovTime2.html
    |    SurgTime2.html
    |
    +---[All]
    |        index-Old.html
    |        main-Old.html
    |        main-Template.html
    |        main.html
    |
    +---[Img]
    |   \---[centers]
    |           AAA.jpg
    |           XYZ.gif
    \---[NewCenterTemplateFolder]
        |
        +---[Download]
        +---[Month]
        +---[MonthCumul]
        +---[Quarter]
        |    index.html
        \    main-Old.html
```

FIGURE 6

| Name of field | Allowed values | Description |
|---|---|---|
| CalculationDate | mm/dd/yyyy | The report system works in the following way: by default, it determines the current periods for Quarterly and Monthly reports using the current system date. For example, when you run the report system on 9/30/1999 as the "current month" for reports, it uses the 8th month (August) and as the "current quarter" it uses the 3rd quarter (from June to August). SOIX generates reports on the 15th day of each month and this does not create any problems, but if one of the centers requests to generate reports before the 15th day but after the 1st day of a month then in this case, by default, the report system will use the previous month as the "current month". And this is not what we want because it is too early to generate the new reports (there is no patient interview records for most medical records) – we just want to recalculate the existing reports. So, to solve this problem, this parameter was introduced. If this parameter has empty value then SOIX report system uses the system date as the "current date", if it is not empty then it uses a value of this parameter. Also this parameter is required to generate sample reports. There is a special version of "soix.mdb" file for sample reports. All records in this database are dated before June 1999, so if the system date is used as the datum then only reports for previous periods can be generated, but if you make the CalculationDate equal to any day in June then May is treated as the "current month". |
| MinNumberOfCases | Integer | Only procedures that have "MinNumberOfCases" or more cases are shown in the "The Executive Benchmark Table" and in the paper reports. |
| Confidence | Real | This is a coefficient before standard deviation to calculate tolerable limits. |
| FoundationDate | mm/dd/yyyy | This date is used as the beginning date for the cumulative reports. |
| QuarterlyReports | Yes, No | Generate quarterly reports? |
| QuarterStart | 1,2,3,4 | Beginning quarter for quarterly reports |
| QuarterYearStart | yyyy | Beginning year for quarterly reports |
| QuarterEnd | 1,2,3,4 | End quarter for quarterly reports |
| QuarterYearEnd | yyyy | End year for quarterly reports |
| MonthlyReports | Yes, No | Generate "current month reports"? |
| MonthStart | 1-12 | Beginning month for "current month reports" |
| MonthYearStart | yyyy | Beginning year for "current month reports" |
| MonthEnd | 1-12 | End month for "current month reports" |
| MonthYearEnd | yyyy | End year for "current month reports" |
| CumulativeMonthlyReports | Yes, No | Generate "cumulative reports"? |
| CumulativeMonthStart | 1-12 | Beginning month for "cumulative reports" |
| CumulativeYearStart | yyyy | Beginning year for "cumulative reports" |
| CumulativeMonthEnd | 1-12 | End month for "cumulative reports" |
| CumulativeYearEnd | yyyy | End year for "cumulative reports" |
| RunMode | | Currently this parameter is not used. |
| CleanedDBF | | Currently this parameter is not used. |
| StandardReport | Yes, No | Currently this parameter is not used. |
| StartDate | mm/dd/yyyy | Currently this parameter is not used. |
| EndDate | mm/dd/yyyy | Currently this parameter is not used. |

FIGURE 7

| Name of field | Allowed values | Description |
|---|---|---|
| colspan Shared parameters that are used by all modules. | | |
| INIPath | A path to a directory. | A path to the folder where INI config files are located. |
| LogPath | A path to a directory. | A path to the folder where LOG files will be created. |
| MDBFile | Full path to a file | Full path to the report master database. |
| LSTPath | A path to a directory. | A path to the folder where LST files are located. |
| OMS2ArchiveDirectory | A path to a directory. | This parameter was used when OMS 2.0 was used as a front end, so now the parameter is not used. |
| OMS2BackupDirectory | A path to a directory. | This parameter was used when OMS 2.0 was used as a front end, so now the parameter is not used. |
| TemplateDirectory | A path to a directory. | A path to the folder where HTML template files are located. |
| UploadDirectory | A path to a directory. | A path to the folder where centers upload incremental files. |
| InternetDirectory | A path to a directory. | A path to the folder where centers reports are located. |
| Parameter used by the paper report modules only | | |
| NewReportsInternetDirectory | A path to a directory | A path to the folder where new reports will be generated. This parameter was introduced as the report generation process takes a lot of time and there is a probability that centers may access their reports during this process. In this situation centers will not be able access their reports at least, but at the same moment there is a probability that these actions may interrupt the report generation process. |
| SavePathForPaperReport | A path to a directory | This parameter points to the path where paper report will be generated. |
| Target | "Web" or "Folder" | This parameter defines the way in which the paper report will be generated. When it is equal to "Folder" than these reports are placed in the separate folder defined by "SavePathForPaperReport" parameter. If this parameter is equal to "Web" than the paper report files will be placed in the centers folders like the modules that generate web-reports do. This option allows to make these reports available for the access trough the Internet. |
| Parameters used by "New_Center_Prepare" module | | |
| NTSecDirectory | Name of folder | This parameter defines a name of the folder where programs from the NTSEC pack are located. These programs are used to set up Windows NT permissions for the centers' upload folders. |
| ApacheUsersFile | Full path to a file. | This parameter defines a full path to apache users file that will created from scratch by the "New_Center_Prepare" module. |
| ApacheUsersFile | Full path to a file. | This parameter defines a full path to Apache users file that will created from scratch by the "New_Center_Prepare" module. This file is used to restrict an access to member sites. |
| ApacheGroupsFile | Full path to a file. | This parameter defines a full path to an Apache groups file that is used to restrict an access to member sites. |
| NewCenterTemplateFolder | A path to a folder | This parameter points to a directory where template files are stored. These files are used to create sites for new centers. |
| PrepareUploadStuff | "Yes" or "No" | Prepare "upload" folder for a new center? |
| PrepareDownloadStuff | "Yes" or "No" | Prepare "download" folder for a new center? |
| PrepareHTMLFiles | "Yes" or "No" | Prepare index HTML files for a new center? |

FIGURE 8

| Name of field | Allowable value | Description |
|---|---|---|
| Indicator_Name | The same restrictions as whose for field name in MS Access | This is a name of the indicator, this name is used for internal purposes of "Executive_Table" module and as a link to the HTML file that describes the indicator. In Fig. 5, the label number 2 shows the place where this text is used. Some HTML tags may be used (Example: <br>, <i>, <font>), as this text is inserted directly in html files without any parsing. |
| Numerator | the name of a field from "*_dump.mdb" tables | This field is used as the numerator to calculate an indicator. Expression that is used to calculate indicators is the following: Indicator = Numerator/Denominator*100% |
| Denominator | the name of a field from "*_dump.mdb" tables | This field is used as the denominator to calculate an indicator. Expression that is used to calculate indicators is the following: Indicator = Numerator/Denominator*100% |
| Description | any text string | Description of the indicator. In Fig. 5, the label number 1 shows the place where this text is used. Some HTML tags may be used (Example: <br>, <i>, <font>), as this text is inserted directly into html files without any parsing. |
| MinOrMax | "Min", "Max" | Use "Min" for indicators that should be minimized and "Max" for indicators that should be maximized. |
| Link | a path to a html file | A path to the html file that describes this indicator. (Example: "/genrep/ind1.html") |

FIGURE 9

| Name of field | Allowable value | Description |
|---|---|---|
| Name_of_Table | Any text | Name of a table. In Fig. 6, the label number 1 shows the place where this text is used. Some HTML tags may be used (Example: <br>, <i>, <font>), as this text is inserted directly into an HTML file without any parsing. |
| Total_by_Proc_Flag | "TotByProc", "" | If this field equals to "TotByProc" then the last row "Total by Procedure" is calculated for this table, if this field is empty then this last row is not calculated. See Fig 6 labels 2. |

| Name of field | Allowable value | Description |
|---|---|---|
| Name_from_Dump_DB | the name of a field from "*_dump.mdb" tables | Module DataTable_Creator takes the value of Name_from_Dump_DB field in "*_dump.mdb" table and puts this value into the table without any modifications and calculations. |
| Row_Name | Any text | Name of a row. On Fig. 6 label number 3 shows the place where this text is used. Some HTML tags may be used (Example: <br>, <i>, <font>), as this text is inserted directly into an HTML file without any parsing. |

FIGURE 10

ANESTHESIA
Site: Sample Center (SMP)
Date of Procedure: 01/01/1999 - 03/31/1999
(Table was created on 06/30/1999)

|  | Arthroscopy, Knee | Carpal Tunnel | Cataract Removal | GI Endoscopy | Laparoscopy, Gyne | Total |
|---|---|---|---|---|---|---|
| General | 139 | 3 | 0 | 0 | 34 | 176 |
| Spinal | 11 | 0 | 0 | 0 | 0 | 11 |
| IV/Local-MAC | 0 | 8 | 63 | 91 | 0 | 162 |
| Local | 0 | 5 | 1 | 0 | 0 | 6 |
| Other | 0 | 33 | 0 | 0 | 0 | 33 |
| Total by Procedure | 150 | 49 | 64 | 91 | 34 | 388 |

PAIN AND COMPLICATIONS
Site: Sample Center (SMP)
Date of Procedure: 01/01/1999 - 03/31/1999
(Table was created on 06/30/1999)

|  | Arthroscopy, Knee | Carpal Tunnel | Cataract Removal | GI Endoscopy | Laparoscopy, Gyne | Total |
|---|---|---|---|---|---|---|
| No Pain, No Complications | 123 | 45 | 62 | 87 | 10 | 327 |
| Pain | 17 | 4 | 2 | 3 | 23 | 49 |
| Nausea | 12 | 0 | 0 | 1 | 4 | 17 |
| Vomiting | 6 | 0 | 0 | 0 | 2 | 8 |
| Instability Of Vital Signs | 1 | 0 | 0 | 1 | 0 | 2 |
| Respiratory Problems | 0 | 0 | 0 | 0 | 1 | 1 |

FIGURE 11

| Name of field | Allowable value | Description |
|---|---|---|
| With_Tolerance | the name of a HTML file without extension or nothing | The HTML file must be in the [SOIX_Report_Sytem]\[Template] folder. If this field is empty then the version with tolerance limits of this report is not generated. In the section where folder [SOIX_Report_Sytem]\[Template] is described you can find more information about internal structure of template files. (Example: for "General Indicators" reports with tolerance zone the template file is "ind.html", so With_Tolerance field equal "ind". |
| Without_Tolerance | the name of a HTML file without extension or nothing | The HTML file must be in the [SOIX_Report_Sytem]\[Template]. If this field is empty then the version with tolerance limits of this report is not generated. In the section where folder [SOIX_Report_Sytem]\[Template] is described you can find more information about internal structure of template files. (Example: for "General Indicators" reports without tolerance zone the template file is "ind2.html", so With_Tolerance field equal "ind2". |
| Chart_Header | Any text | This text is used as a header in the report chart. See Fig. 7, label 1. To insert "Enter" in this string use "‖" (double vertical bar). Also values of the fields from "*_dump.mdb" tables and values of all indicators calculated inside Chart_Generator module can be used. To use them, use the following format: %Name_Of_FieldThisSite% for current center and %Name_Of_FieldAllSites% for all centers (Example: Total Medical Records field has the name TotMR, so placeholders for it will be %TotMRThisSite% and %TotMRAllSites%). In each section of Indicators.1st file, a user assigns names for each indicator that is calculated by Chart_Generator module – although these names and values of indicators are not saved anywhere, you can still use them in Chart_Header field (Example: In section "General Indicators" indicator with name "ind1" is defined, so you can use placeholders %ind1AllSites% and %ind1ThisSite%.) |
| Chart_Footer | Any text | This text is used as a footer in the report chart. See Fig. 7, label 2. All instruction for Chart_Header field can be used for this field. |

FIGURE 12

| Name of field | Allowable value | Description |
|---|---|---|
| Indicator_Name | The same restrictions as whose for field name in MS Access | Used for internal calculations only. Make sure that there is no any field in "*_dump.mdb" files with the same name. |
| Numerator | the name of a field from "*_dump.mdb" tables | This field is used as the numerator to calculate the indicator. The expression that is used to calculate indicators is the following:<br>Indicator = Numerator/Denominator*100% |
| Denominator | the name of a field from "*_dump.mdb" tables | This field is used as the denominator to calculate the indicator. The expression that is used to calculate indicators is the following:<br>Indicator = Numerator/Denominator*100% |
| AxesLabels | Any text | This text is used in charts as label of the indicator. To put "*" character use double caret characters ("^^"). See Fig. 7 label 3. |

Recovery Time

|  | 0-29 | 30-59 | 60-89 | 90-119 | 120-149 | 150-179 | 180-209 | 210-239 | 240+ |
|---|---|---|---|---|---|---|---|---|---|
| All Sites: | | | | | | | | | |
| Ratio | 8.9 | 19.0 | 58.0 | 10.9 | 2.0 | 0.0 | 0.0 | 0.0 | 1.2 |
| Cases for Given Range | 44 | 94 | 287 | 54 | 10 | 0 | 0 | 0 | 6 |
| Total Cases: 495 | | | | | | | | | |
| Your Site: | | | | | | | | | |
| Ratio | 16.7 | 14.6 | 54.2 | 12.5 | 2.1 | 0.0 | 0.0 | 0.0 | 0.0 |
| Cases for Given Range | 8 | 7 | 26 | 6 | 1 | 0 | 0 | 0 | 0 |
| Total Cases: 48 | | | | | | | | | |

FIGURE 14

| Name of field | Allowable value | Description |
|---|---|---|
| Numerator | the name of a field from "*_dump.mdb" tables | This field is used as a denominator to calculate the indicator. The expression that is used to calculate indicators is the following:<br>Indicator = Numerator/Denominator*100% |
| Denominator | the name of a field from "*_dump.mdb" tables | This field is used as the denominator to calculate the indicator. The expression that is used to calculate indicators is the following:<br>Indicator = Numerator/Denominator*100%. If Denominator is empty then Numerator is used only and the expression becomes as Indicator=Numerator |
| Descipting_Text | Any text | Name of a row. In Fig. 8, the label number 2 shows the place where this text is used. Some HTML tags may be used (Example: <br>, <I>, <font>), as this text is inserted directly into an HTML file without any parsing. |

FIGURE 15

Comparison Table - Sample Center

| | | | | Arthroscopy, Knee | | GI Endoscopy | | Cataract Removal | | Carpal Tunnel | | Laparoscopy, Gyne | |
|---|---|---|---|---|---|---|---|---|---|---|---|---|---|
| 3 | 2 | 1 | | Your Center | All Centers | Your Center | All Centers | Your Center | All Centers | Your Center | All Centers | Your Center | All Centers |
| Number of Patients | | | | 150 | 1269 | 91 | 1372 | 64 | 856 | 49 | 505 | 34 | 388 |
| Time (Minutes) | | | | | | | | | | | | | |
| Time For Procedure | | | | 37 | 46 | 176 | 124 | 27 | 26 | 16 | 52 | 31 | 99 |
| Time For Recovery | | | | 98 | 184 | 657 | 454 | 29 | 30 | 63 | 132 | 111 | 362 |
| Time For Patient Interview | | | | 4 | 4 | 3 | 3 | 2 | 2 | 4 | 4 | 3 | 3 |
| Problems Before Leaving Surgery Center | | | | | | | | | | | | | |
| Percent Normal Discharge | | | | 100.0 | 99.5 | 100.0 | 100.0 | 100.0 | 100.0 | 100.0 | 100.0 | 100.0 | 100.0 |
| Percent without Problems | | | | 82.0 | 84.9 | 95.6 | 97.1 | 96.9 | 96.6 | 91.8 | 95.0 | 29.4 | 36.6 |
| Percent with Post Operative Pain | | | | 53.3 | 61.2 | 2.2 | 1.5 | 4.7 | 5.3 | 18.4 | 14.9 | 67.6 | 60.1 |
| Percent Medications Ordered | | | | 100.0 | 100.0 | 50.0 | 50.0 | 100.0 | 100.0 | 100.0 | 100.0 | 100.0 | 100.0 |
| Percent Pain Relieved | | | | 96.3 | 97.7 | 50.0 | 50.0 | 66.7 | 71.1 | 100.0 | 96.0 | 100.0 | 100.0 |
| Percent Pain Prescription Given | | | | 99.3 | 99.0 | 2.2 | 1.5 | 3.1 | 3.0 | 100.0 | 97.6 | 91.2 | 90.7 |

FIGURE 16

| Name of field | Allowable value | Description |
|---|---|---|
| Field_Name | the name of a field from "*_dump.mdb" tables | Use only fields that contain absolute number of cases. In current version of the report system almost all fields satisfy this restriction – only the fields with average times do not satisfy. |
| Descipting_Text | Any text | Name of the column. In Fig. 9 , the label number 1 shows the place where this text is used. Some HTML tags may be used (Example: <br>, <i>, <font>), as this text is inserted directly into an HTML file without any parsing. |

FIGURE 17

Case Distribution
Date of Procedure: 03/01/1999 - 10/31/1999
Table was created on 11/16/1999          1

| Procedure Name | Center | Medical Records | Patient Interview |
|---|---|---|---|
| Arthroscopic ACL Repair (1 center) | QCA | 2 | 2 |
| | Total | 2 | 2 |
| Breast augmentation (3 centers) | AAM | 10 | 10 |
| | AAS | 19 | 15 |
| | RSA | 1 | 1 |
| | Total | 30 | 26 |
| | AAD | 47 | 47 |
| | AAE | 14 | 14 |
| | AAL | 8 | 8 |
| | AAS | 10 | 5 |
| Rhinoplasty (2 centers) | | | |
| | Total | 10 | 9 |
| | AAE | 1 | 1 |
| | AAM | 3 | 3 |
| Rhytidectomy (4 centers) | AAS | 1 | 1 |
| | RSA | 1 | 1 |
| | Total | 6 | 6 |
| Grand Total | | 4,999 | 4,581 |

FIGURE 18

| Name of field | Allowable value | Description |
|---|---|---|
| Name_of_Field_1 | The same restrictions as whose for field name in MS Access | When you select a name for this field, make sure that this field must be unique among fields in MEDREC table, PATINT2 table and fields defined in Stage1.1st and Stage2.1st files. |
| SQL_Expression | Expression in MS SQL language | Use help files for MS Access or Visual Basic to get additional information about MS SQL language. In SQL_Expression field, you can use Name_of_Field_1 fields from other strings of Stage1.1st file, but be careful and do not create an unsolvable situation when in the current string you use another field, but the SQL_Expression for that field uses Name_of_Field_1 for the current string. This is so called "Circular reference". |

FIGURE 19

| Name of field | Allowable value | Description |
|---|---|---|
| Name_of_Field_2 | The same restrictions as whose for field name in MS Access | When you select a name for this field, make sure that this field must be unique among fields in MEDREC table, PATINT2 table and fields defined in Stage1.1st and Stage2.1st files. |
| Data_Type_of_Field | Text, Long, Single | Defines a type of the field. Currently three data types are supported but this list can be easily expanded. |
| SQL_Expression | Expression in MS SQL language | Use help files for MS Access or Visual Basic to get additional information about MS SQL language. Inside the SQL_Expression you can use Name_of_Field field from other strings of Stage1.1st file, but be careful and do not create an unsolvable situation when in current string you use another field, but SQL_Expression for that field uses Name_of_Field of current string. |
| Denominator | Any item from the Name_of_Field_2 list | Most of the fields from Name_of_Field_2 list are absolute numbers of cases, so to get a value for the whole industry, values for different centers must be just summed up. Some of the fields like average times are not applicable to this rule, they contain relative values, so a simple addition cannot be used to calculate the whole industry values. In this case the following mathematical expression is used: $$Ind_{All} = \frac{\sum_{k=1}^{N}(Ind_k \times Denom_k)}{Denom_{All}},$$ where $Ind_{All}$ – value for the whole industry, $Ind_k$ – value for $k$ center, $Denom$ – denominator for the field. So Denominator defines a field that is the denominator for a given indicator. If Denominator is empty then an ordinary addition is used. |

FIGURE 22

Benchmarking Report

The diagram below shows the *level* of the indicator achieved in YOUR CENTER as a wide white bar.
The AVERAGE level at *all the participating centers* is shown as a blue bar.

The values of the indicators shown with small letters (ind1 thru ind5) should be minimal
The values of the indicators shown with CAPITAL letters (IND6 thru IND10) should be maximal

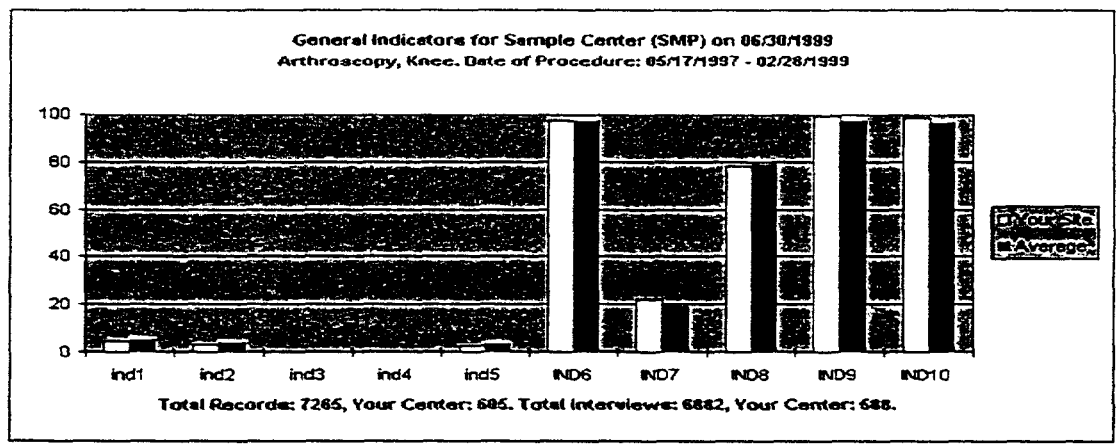

- ind1 = Perioperative Complications
- ind2 = Delayed in Discharge
- ind3 = Returns to Surgery
- ind4 = Admits to Hospital
- ind5 = Pain Episodes Not Relieved
- IND6 = Care Not Needed After Discharge
- IND7 = Pain Controlled After Discharge
- IND8 = Satisfied Patients
- IND9 = Effective Discharge Instructions
- IND10 = Patients Prepared for Self-Care

|  | ind1 | ind2 | ind3 | ind4 | ind5 | IND6 | IND7 | IND8 | IND9 | IND10 |
|---|---|---|---|---|---|---|---|---|---|---|
| All Sites: | | | | | | | | | | |
| Indicator | 5.5 | 4.3 | 0.0 | 0.0 | 3.7 | 97.2 | 18.7 | 78.5 | 97.1 | 96.4 |
| Numerator | 398 | 311 | 0 | 0 | 178 | 6688 | 873 | 5399 | 6685 | 6637 |
| Denominator | 7265 | 7265 | 7265 | 7265 | 4804 | 6882 | 4667 | 6882 | 6882 | 6882 |
| Your Site: | | | | | | | | | | |
| Indicator | 4.8 | 2.8 | 0.0 | 0.0 | 2.3 | 97.1 | 22.1 | 78.4 | 98.6 | 98.1 |
| Numerator | 29 | 17 | 0 | 0 | 10 | 571 | 90 | 461 | 580 | 577 |
| Denominator | 605 | 605 | 605 | 605 | 427 | 588 | 407 | 588 | 588 | 588 |

Surgery Time

The diagram below shows the *level* of the indicator achieved in YOUR CENTER as a wide white bar.
The AVERAGE level at *all the participating centers* is shown as a blue bar.

|  | 0-29 | 30-59 | 60-89 | 90-119 | 120-149 | 150-179 | 180-209 | 210-239 | 240+ |
|---|---|---|---|---|---|---|---|---|---|
| All Sites: | | | | | | | | | |
| Ratio | 28.5 | 37.6 | 21.3 | 7.9 | 2.0 | 1.2 | 1.1 | 0.0 | 0.4 |
| Cases for Given Range | 717 | 945 | 536 | 199 | 50 | 29 | 27 | 0 | 10 |
| Total Cases: 2513 | | | | | | | | | |
| Your Site: | | | | | | | | | |
| Ratio | 24.4 | 35.0 | 25.4 | 9.6 | 2.5 | 1.0 | 1.5 | 0.0 | 0.5 |
| Cases for Given Range | 48 | 69 | 50 | 19 | 5 | 2 | 3 | 0 | 1 |
| Total Cases: 197 | | | | | | | | | |

# PERFORMANCE OUTCOMES BENCHMARKING

CROSS-REFERENCE TO RELATED APPLICATIONS

This patent application claims priority to U.S. Provisional Patent Application No. 60/252,129, filed Nov. 21, 2000, which is hereby incorporated by reference herein in its entirety.

FIELD OF THE INVENTION

The present invention relates generally to creation and management of feedback reports for a benchmarking process and, more particularly, to a technique for acquiring primary data at the source, compiling the data in an analytically meaningful manner for benchmarking, preparing web based reports and maintaining and managing cumulative historical data and reports.

BACKGROUND OF THE INVENTION

Benchmarking which is a comparison of performance outcomes from a process to a norm is a useful tool for measuring quality and developing methods of improving a process.

One example of an area in which benchmarking is particularly useful is in monitoring ambulatory surgery procedures. Professional organizations have made attempts to acquire and tabulate ambulatory surgical procedures outcomes data for benchmarking. These attempts have suffered three deficiencies. First the data is typically taken from secondary sources such as billings or claims records and not from the patient. Second, uniform criteria are not applied in obtaining the data collection. Third, data is typically compiled and distributed in a hard copy form and cannot be accessed in a convenient internet dispersed form.

SUMMARY OF THE INVENTION

In view of the foregoing it would be desirable to provide a technique for collecting, evaluating and reporting outcomes data for the purposes of benchmarking which overcomes the above described inadequacies and shortcomings. More particularly it would be desirable to provide a technique for collecting outcomes data at a primary level, evaluating the data in an analytically meaningful manner reporting the outcome data and maintaining historical data for generation of future comparisons in an efficient and cost effective manner. It is particularly desirable that such a system be computer based and use a network such as the internet both for transporting input data and disseminating reports.

According to the present invention, a technique for performance outcomes benchmarking is provided. In one exemplary embodiment, the technique is realized by a method for outcomes monitoring comprising the steps of: collecting at least two outcomes data sets; converting the at least two outcomes data sets into an at least one outcomes result; establishing a norm for an outcomes data group, the outcomes data group comprising a plurality of the at least two outcomes data sets; comparing a selected one of the at least one outcomes result to the norm; and generating at least one outcomes monitoring report comprising the selected one of the at least one outcomes result and the norm.

In accordance with other aspects of this exemplary embodiment, the method may further include: transmitting the at least two outcomes data sets to a data processor; selectively restricting access to the outcomes monitoring report; posting the outcomes monitoring report to a webpage or selectively restricting access to the webpage or a combination thereof.

In accordance with other aspects of this exemplary embodiment, the outcomes data sets may be collected from at least one user entity at a plurality of discrete intervals and the outcomes report may be prepared from the outcomes data collected at least two of the plurality of discrete intervals.

In accordance with further aspects of this exemplary embodiment, the outcomes data sets may be collected from a plurality of user entities; outcomes data sets for each user entity of the plurality of user entities individually identified and converted. The outcomes data sets from the plurality of user entities may comprise the outcomes data group.

In accordance with further aspects of this exemplary embodiment the outcomes monitoring report includes at least one outcomes result for a selected user entity of the plurality of user entities and at least one comparison of the norm to the selected one of the at least one outcomes result for the selected user entity.

In accordance with additional aspects of this exemplary embodiment, the embodiment includes a computer signal embodied in a carrier wave readable by a computing system and encoding a computer program of instructions for executing a computer process performing the method for outcomes monitoring described herein.

In another exemplary embodiment a technique for monitoring surgical procedure outcomes is provided. In one exemplary embodiment the technique is realized by a method for outcomes monitoring of surgical procedures comprising the steps of: collecting at least two primary source surgical outcomes data sets; converting the at least two primary source surgical outcomes data sets into at least one outcomes result; establishing a norm for an outcomes data group, the outcomes data group comprising a plurality of the at least two outcomes data sets, comparing a selected one of the at least one outcomes result to the norm; and generating at least one outcomes monitoring report comprising the selected one of the at least one outcomes result and the norm.

In accordance with other aspects of this exemplary embodiment the Method may further include: transmitting the at least two primary source surgical outcomes data sets to a data processor; selectively restricting access to the outcomes monitoring report; posting the outcomes monitoring report to a webpage; and selectively restricting access to the webpage.

In accordance with other aspects of this exemplary embodiment the method may further include collecting the at least two primary source surgical outcomes data sets from a plurality of surgical centers; and individually identifying and converting the at least two primary source outcomes data sets for each surgical center of the plurality of surgical centers where the outcomes data sets from the plurality of surgical centers comprises the outcomes data group.

In accordance with other aspects of this exemplary embodiment the method may further include an outcomes monitoring report which has at least one outcomes result for a selected surgical center of the plurality of surgical centers and at least one comparison of the norm to the selected one of the at least one outcomes result for the selected surgical center.

In accordance with further aspects of this exemplary embodiment, the embodiment may include a computer signal embodied in a carrier wave readable by a computing system and encoding a computer program of instructions for executing a computer process performing the method for outcomes monitoring of surgical procedures described herein.

In another exemplary embodiment an apparatus for outcomes monitoring is provided. The apparatus comprises: a data collection portion wherein the data collection portion collects at least two outcomes data sets; a data processor portion wherein the data processor portion receives the at least two outcomes data sets from the data collection portion and wherein the data processor comprises: a converter portion wherein the converter portion converts the at least two outcomes data sets into an at least one outcomes result; a norm establishing portion wherein the norm establishing portion establishes a norm for an outcomes data group, the outcomes data group comprising a plurality of the at least two outcomes data sets, a comparison portion wherein the comparison portion compares a selected one of the at least one outcomes result to the norm; and a report generation portion wherein the report generation portion generates at least one outcomes monitoring report comprising the selected one of the at least one outcomes result and the norm.

In accordance with further aspects of this exemplary embodiment, the apparatus for outcomes monitoring may further comprise a webpage portion wherein the at least one outcomes monetary report is posted to a webpage; or a security portion, the security portion selectively restricting access to the at least two outcomes data sets, the at least one outcomes result and the at least one outcomes monitoring report; or both.

In accordance with other aspects of this exemplary embodiment, the apparatus for outcomes monitoring may be an apparatus wherein the at least two outcomes data sets are surgical procedures outcomes data sets, or wherein the at least two surgical procedures outcomes data sets are primary source data sets or both.

The present invention will now be described in more detail with reference to exemplary embodiments thereof as shown in the appended drawings. While the present invention is described below with reference to preferred embodiments, it should be understood that the present invention is not limited thereto. Those of ordinary skill in the art having access to the teachings herein will recognize additional implementations, modifications, and embodiments, as well as other fields of use, which are within the scope of the present invention as disclosed and claimed herein, and with respect to which the present invention could be of significant utility.

BRIEF DESCRIPTION OF THE DRAWINGS

In order to facilitate a fuller understanding of the present invention, reference is now made to the appended drawings. These drawings should not be construed as limiting the present invention, but are intended to be exemplary only.

FIG. 3 is a exemplary up load screen in accordance with one embodiment of the invention;

FIG. 4 is an exemplary report in accordance with one embodiment of the invention;

FIG. 5 shows a flow chart for the report system structure in accordance with one embodiment of the invention;

FIG. 6 shows exemplary parameters for a file for defining report periods in accordance with one embodiment of the invention;

FIG. 7 shows exemplary parameters for a file which provides paths to different components of a report system in accordance with one embodiment of the invention;

FIG. 8 shows an example of the parameters associated with an executive table list file in accordance with one embodiment of the invention;

FIG. 9 show an example of a data table items file parameters in accordance with one embodiment of the invention;

FIG. 10 shows an example of a data table in accordance with one embodiment of the invention;

FIG. 11 shows an example of parameters for general report sections in accordance with an embodiment of the invention;

FIG. 12 shows an example of parameters of an indicators description string in accordance with an embodiment of the invention;

FIG. 14 shows an example of parameters of a comparison table file in accordance with one embodiment of the invention;

FIG. 15 shows a report of the type showing data for a user and cumulative data for all user groups used in establishing a norm in accordance with one embodiment of the invention;

FIG. 16 shows the parameters of a ProcDistrib file in accordance with one embodiment of the invention;

FIG. 17 shows a case distribution table in accordance with one embodiment of the invention;

FIG. 18 shows an exemplary first stage list file in accordance with one embodiment of the invention;

FIG. 19 shows an exemplary second stage list file in accordance with one embodiment of the invention;

FIG. 22 is an exemplary graphic report in accordance with one embodiment of the invention.

DETAILED DESCRIPTION OF EXEMPLARY EMBODIMENTS

The outcomes monitoring system (OMS) of the invention (also referred to herein as the System) is described in the context of collecting and reporting outcomes data for benchmarking ambulatory surgical procedures which may be used for benchmarking both a given center's performance for a particular procedure(s) against historical data for that surgery center or for benchmarking the performance of a particular center with respect to the performance of a group of centers. As used herein a center is a user unit entity such as a clinic, or a business for example. The term "user" includes both the user entities as well as the human beings using the system. As one skilled in the art will appreciate this is one example of the usefulness of the invention. The invention may be applied in other areas of healthcare, such as, the benchmarking of hospital, nursing home, student health center or abortion clinic procedures, for example.

Further the invention may be generally applicable to benchmarking performance in such areas as sales force performance, customer satisfaction, manufacturing process performance, service provider performance and the like. As one of ordinary skill in the art will appreciate the outcome monitoring system of the invention may be used for benchmarking performance in these areas and other areas without undue experimentations. Further, the invention accommodates benchmarking from primary data (e.g., information directly acquired from individuals involved in the process such as patients, health care providers, or customers and the like or measurements made or data taken as a direct result of the process). For example, or secondary data such as billing records or claims records, for example, or a combination thereof. The ability to obtain benchmarking information from a primary source while maintaining confidentiality or privacy of specific identifiers for the primary source is a particularly desirable feature of some embodiments of the invention.

At this point it should be noted that the system in accordance with the present invention as described herein typically involves the processing of input data and the generation of output data to some extent. This input data processing and output data generation may be implemented in hardware or software. For example, specific electronic components may be employed in a personal computer, server or similar or related circuitry for implementing the functions associated with acquiring, transmitting, analyzing and storing data in accordance with the present invention as described herein. Alternatively, one or more processors operating in accordance with stored instructions may implement the functions associated the system in accordance with the present invention as described herein. If such is the case, it is within the scope of the present invention that such instructions may be stored on one or more processor readable media, or transmitted to one or more processors via one or more signals.

Figure 1:
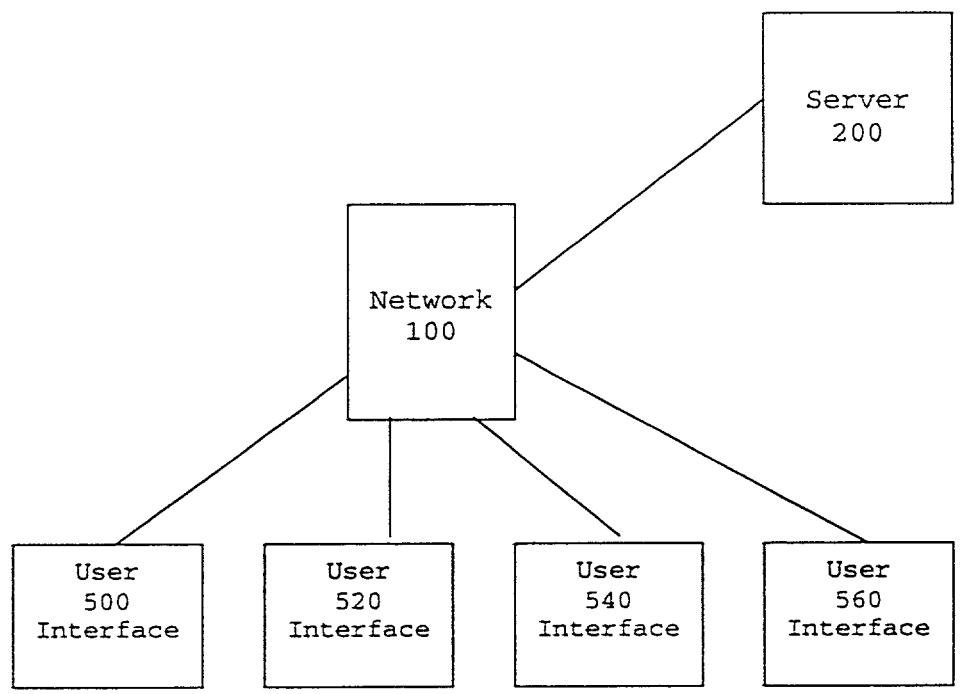
FIG. 1 is a schematic diagram of the system of the invention in accordance with the present invention.

Referring to FIG. 1, in general the system of the invention comprises a plurality of user interfaces 500, 520, 540, 560, a network 100 and a server 200. Four user interfaces are shown in FIG. 1 as representative of the plurality of user interfaces that may be associated with the system. The number of user interfaces may be greater or less than four. The plurality of user interfaces are personal computers (PC) equipped with modems and suitable software in an exemplary embodiment. More particularly suitable user interfaces 500, 520, 540, 560 may, for example, include an IBM-PC compatible personal computer capable to run under Windows-95 (or 98) operating system, a Pentium processor with clock speed more than 100 MHz, 16 MBytes (or higher) of RAM, 1000 MByte (or higher) hard disk capacity; a dial-up Internet connection with an Internet service provider; a 28.8 (or higher) kbps telephone modem for data transfer; (optionally) a lower speed modem for automated patient interview dialing, which requires a second telephone line; and the database management system such as FileMaker Pro or Visual Basic.

Additionally, the user interfaces 500, 520, 540, 560 will have performance outcomes benchmarking software as described herein. Further, it is desirable that the user interfaces 500, 520, 540, 560 have a means for archiving data such as a floppy disk or CD or the like or be linked to a suitable memory device for archiving data obtained at the user site.

The user interfaces 500, 520, 540, 560 are used for collecting data and inputting data into the system and accessing reports generated by the system. Further, as illustrated in FIG. 1 the user interfaces 500, 520, 540, 560 are not directly interconnected. This is preferable in embodiments where highly confidential information is involved such as when the users are competitors or when personal confidential information such as patient identity is involved, for example. In such cases, it is important to restrict access of a particular user to that user's data and results, and that user's results as compared to compiled benchmarking norms for all users.

As FIG. 1 shows the user interfaces 500, 520, 540, 560 are connected to a network 100. The network 100 is used to transmit data collected and input by the users to the server and disseminate the analyzed data and reports to the user. In an exemplary embodiment, the network 100 is a general access network such as the Internet, for example. Confidentiality of information transmitted over the network 100 may be maintained by the use of such known means as password protection and encryption, for example. In preferred embodiments reports are posted to a password protected web page or the like.

The server 200 processes the collected data transmitted via the network 100, prepares reports and archives data and reports. The algorithms of this invention typically reside in the server 200. The algorithms are applied to analyze the collected data which in turn yields results suitable for comparisons of performance. The comparisons may be internal to a particular user such as comparison of the performance of one month to the performance of another month, for example, or may compare the user's performance for a specified period to a norm based on an average for a group of users. The results may be considered to be statistically significant if based on a data group (as used herein a data group is a plurality of discrete data sets) of a suitable size. Typically, at least 30 data points are used for calculating statistically significant results. Reports reflecting the results of the data analysis are generated in the server 200. In an exemplary embodiment results are stored in tables such that reports customized in content and form may be generated in a facile manner. The collected data, analyzed results and reports or a combination thereof are also archived in the server 200 or alternatively in a memory device associated with the server. Hence not only may previous reports be accessed, but also collected data and analyzed results are available for use in generating future reports. For example it is frequently desirable to compare existing data with new data as it becomes available.

In an exemplary embodiment, the server used to operate an Outcomes Monitoring System may be a Hewlett Packard NetServer LH 3. The HP Server contains 5 hard drives which are used for the storage of data and the programs required for operation. In conjunction with the HP Server, a Cisco 1720 Router is used to provide the Internet connection. Internet service with a connection speed of 512K is used in this exemplary embodiment. This server is described for illustrative purposes and is one of many servers suitable for use in the outcomes monitoring system of this invention.

Figure 2:
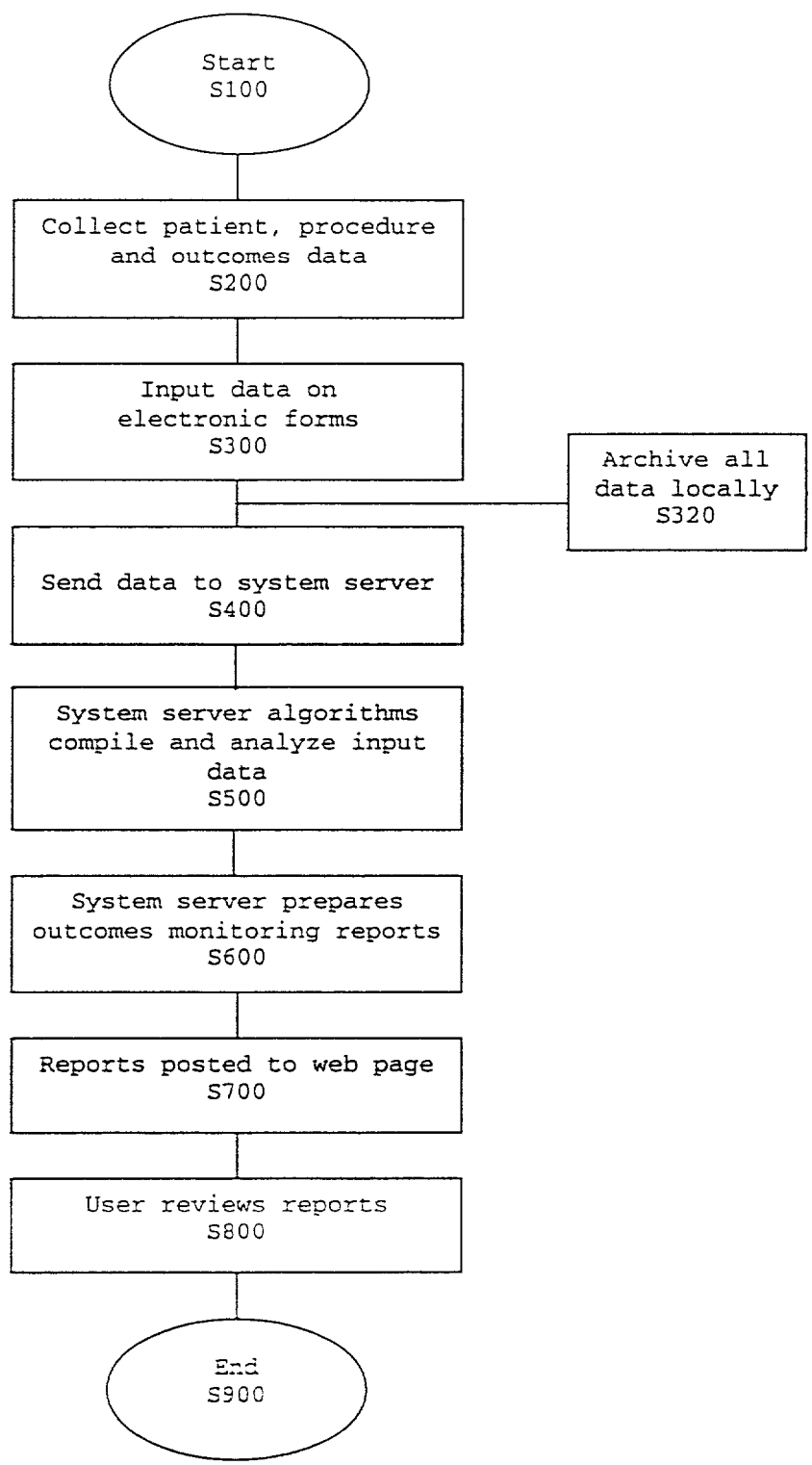
FIG. 2 is a diagram showing the steps of using the invention in accordance with one embodiment of the present invention.

Referring to FIG. 2, use of the invention in an embodiment directed to outcomes monitoring of ambulatory surgical procedures, is summarized. As one skilled in the art will recognize this is one of many possible embodiments related to health care outcomes monitoring. Further, other embodiments of the invention may be applied in many other types of outcomes monitoring of processes including, for example, service performance, sales force performance, service provider performance, manufacturing performance and the like, for example. For convenience, use of the invention is described in terms of outcomes monitoring of ambulatory surgical procedures with the understanding that the fundamental steps of use of the invention are comparable in other embodiments.

As shown in FIG. 2, the steps of using an exemplary embodiment of the invention directed to outcomes monitoring of ambulatory surgical procedures include: collection of patient, procedure and outcomes data S200, input of collected data S300, transmission of data to the system server S400, compilation and analysis of data by system server algorithms S500, preparation of outcomes monitoring (benchmarking) reports by the system server S600, posting of the outcomes monitoring reports to a web page S700, and user review of reports via internet connection to the web page S800. The steps for use of the exemplary embodiment are discussed in further detail below.

Referring to FIG. 2, step S200 comprises collection of patient, procedure and outcomes data (herein collectively referred to as outcomes data set(s). In a preferred embodiment, the data is collected directly from the patient, center staff or both at a time coinciding with the procedure, within a predetermined proximity to the procedure or both.

To maintain patient privacy and confidentiality, patient identification codes may be assigned. A system of patient identification (ID) codes, unique for each episode of care, may be established at each center. In order to maintain complete patient confidentiality, it is preferable that centers not use social security numbers for ID codes. A surgical center may assign a patient a facility specific ID number, with no relation to any personal identification numbers or names. Alternatively, the ID "number" may be derived from another numbering system used by the facility, such as patient account numbers, etc. so long as numbers are not repeated for patients with multiple episodes of care. To protect privacy and confidentiality it is preferable that patient names and medical record numbers are not provided to the server. Maintaining records of specific patient information associated with data entries at a center or local user level is important to the center's ability to address issues identified in the reports of the OMS and apply benchmarking results to improve performance.

Potential OMS participants in the exemplary embodiment are all patients scheduled for an applicable procedure. Participants as used herein are primary data sources. Criteria may be established to identify a suitable primary data source. For example patients in an exemplary embodiment for ambulatory surgical procedure monitoring are typically excluded if they undergo two unrelated procedures simultaneously (example: patient having a cataract removal and hernia repair at the same time);

the patient is scheduled for a planned inpatient admission postoperatively; or none of the procedure codes on the patient's record matches any of the codes included in the identified procedure codes to be benchmarked.

In an exemplary embodiment, centers are strongly encouraged to submit data on as many patients as possible, (20 percent of specified population(s) is suggested) but there are no minimum requirements for data submission. Depending upon the size of the center and the volume of procedures performed, a center may determine its own standards for quantity of data collected. It should be kept in mind, however, that larger databases provide more meaningful information. A minimum of 30 points are desirable for statistically significant evaluation. However, lesser numbers may be useful for identifying quality issues.

Further the system permits benchmarking of a wide range of types of data. Hence many kinds a data may be collected and considerably flexibility is afforded in outcomes that may be monitored and benchmarked. However, for benchmarking a particular outcome it is important to use uniform criteria when collecting data related to that outcome.

In an embodiment for monitoring health care outcome stripping all personal identifiers from the data transmitted to the server is desirable. It may further be desirable to inform patients that:

1. no identifiable medical or personal information will leave the Local Center;
2. that server staff will have no personal identifiers;
3. that only grouped information will be reported back to the center;
4. that participation will not affect the care they receive; and the like.

Additionally, in some cases it may be desirable to obtain informed consent from patient.

Referring again to FIG. 2, step S300 is data input. The data collected will typically be collected as a data set for a particular process such as a surgical procedure, for example. Typically, a data set will include a plurality of responses to a set of indicators. Indicators may be verbal responses; measured analytical data such as times, weights, ages, dosage of medicine and the like, or observations of a third-party observer, for example. Any indicator reflective of the outcome of the process being monitored may be used. Although one indicator may be used, typically a set of indicators will be used. It may be desirable in some embodiments to validate benchmarking indicators utilizing statistical methods known to those of ordinary skill in the art.

The indicators (indicators as used herein are the specific information gathered) may be defined for any process or procedure to be benchmarked. Such indicators may be customized to the procedure or process to be benchmarked.

The specific data collected for comparison purpose should be collected in a standardized manner with specified collection criteria. However, the system provides extensive flexibility in selection of data to be collected. This allows the system to be applied to a range of needs and benching marking of many types of procedures. Further data collection may include questions which are intended for site specific benchmarking in addition to questions which are intended for broader based comparisons. Additionally, questions for general reference such as marketing studies, scientific research studies and the like, may be included and archived for reference, but not utilized in the process of evaluating data and preparing benchmarking reports.

The data collection process may take many forms. The following example is illustrative of the type of information that may be collected and a procedure that may be followed which utilizes standardized criteria. As one skilled in the art will recognize, this is one of many suitable data collection protocols which may be used in the practice of the invention.

Data collection in an Outcomes Monitoring System for Ambulatory Surgical Centers in one embodiment may begin by opening a Medical Record Abstract Form. The form may include input fields such as:

Add A New Record
Patient ID
Procedure Date
Payor
Procedure Information (predefined procedure category, codes facilitate standardization)
Start and end time of the Procedures
Recovery Sites
Discharge Time
Time at which Patient Met Discharge Criteria
Type of Anesthesia (Codes facilitate standardization)
MD Present during anesthesia (yes or no)
Patient Disposition following surgery
Any of a predetermined list of identified problems experienced (problems are defined as well as criteria for assessing significance of a problem and response selections provided)
Postoperative Pain Management (Including yes/no responses to questions such as:
Pain Verbalized?
Med Ordered?
Med Admin?
and Pain Relieved?

Discharge Pain Management (including yes/no questions such as):
  Pain Prescription Given?
  Pain Control Methods Explained?
  and Institution Specific Variables As a general rule, it is desirable for monitoring outcomes of ambulatory surgery procedures that a post-discharge patient interview take place within 1-2 working days from the date of discharge. In an exemplary embodiment this may be a phone interview. It is important that patients be contacted while the events of their care are fresh in their memory. The purpose of the interview is to collect information about the "outcome" of the procedure (i.e. checking the patient's condition after discharge), and to collect information about the patient's perception of their care (i.e. level of satisfaction with the care provided).

The data obtained from the patient telephone interview may be entered in a Patient Telephone Interview form. The form may include such data entry fields as:
  Patient ID, date;
  Time of the interview, patient responses, who was interviewed, and time the interview ended;
  All interviews should begin with an introduction of the caller including the reason for the call.

In order to obtain data that is reliable it is important that all interviewers use the same definitions and questions and responses are recorded using one of the preselected response choices. Types of sample questions and selected responses include:
1. After leaving the surgery center . . . These questions relate to whether—Patients were adequately prepared for self-care at home after discharge and apply to all procedure groups. It is important that the answers to each question are recorded as "yes," "no," or "somewhat." Some patients may need instructions in this regard.
2. At any time after leaving the center did you have . . . These questions relate to Quality—"Patients experiencing problems after discharge related to the surgical procedure requiring medical or surgical care." The "key" words in this indicator are related to the surgical procedure and requiring medical or surgical care. Problems patients report that do not relate to their surgical procedure (i.e. a fall after arriving home; an auto accident on the way home, etc.) should not be considered in question 2 of the interview. Also, only problems that resulted in the patient seeking additional medical care may be considered as "meeting" the indicator. Questions applicable to specific procedure groups may be included.
3. After returning home . . . These questions relate to whether—Patients expressing pain after discharge who had relief of pain after utilizing pain control methods as instructed.
4. How well would you say your pain was relieved . . . This question assess the patients' relief of pain. Patients may be asked to rate their pain on a scale of 1 to 10, with "1" equaling complete relief and "10" not relieved at all.
5. How would you describe the quality of care you received . . . These questions are directed towards determining whether—patients were satisfied with pre-operative, intraoperative, and postoperative care.

For an exemplary embodiment for monitoring ambulatory surgical procedures, outcomes procedures to be monitored and indicators are preferably determined prior to data collection.

In an embodiment for benchmarking ambulatory surgical procedures, patient data is typically collected from patients, patient relatives or surgery center staff or a combination thereof.

In a preferred embodiment electronic forms and tables may be used to enter and compile patient data. As discussed each patient receives a unique ID code, so that data entered at a center may be transmitted to the server without personal identifiers.

Data may be entered directly into electronic screens during medical record reviews and telephone interviews. Alternatively data may be documented as paper records and entered into the electronic system at a later time. Data entry directly from a primary data source into electronic form is preferred. Further in a preferred embodiment data collection forms are based on modifications of instruments that have been validated.

More particularly, data collection and abstracting may be completed in one of two ways:
1. Manually: Blank forms are printed and data is manually entered onto the forms and entered into the computer file at a later time. This method is not generally recommended but can be used.
2. Directly: Data are entered directly into the computer screen. After a sufficient number of records are completed (20 or more, for example), the data may be "uploaded" to server through an Internet connection.

As a center compiles and transmits information, server staff may conduct both overall and center-specific analyses of the clinical data. A center is encouraged to archive all patient data with patient identifiers locally (See S320). Such local archival enables a center to investigate issues identified by the OMS in depth at a later date, e.g., benchmarking identifies trends and follow-up of individual patients may be necessary to establish reasons for deviations from expected values. Thus by monitoring patient specific data at the local level this information which is useful to the center is maintained while the risk of improper invasion of patient privacy is minimized.

Because medical information is rightly held by patients and health care providers to be confidential, effort should be made to assure confidentiality and privacy throughout the system. Entry into the database associated with data input may be controlled via passwords for example, and only personnel directly involved in data entry or supervision should have access to databases to maintain confidentiality of patient data.

Other measures to restrict access to the information contained in the OMS may include physical and electronic barriers to access, restrictions on patient information maintained at the server and reporting only of group results. In embodiments in which data may be stored on the server, the server may be password protected at the user level, and a second password may be required to access the study database. Further in a preferred embodiment the personal identifiers are stripped from the data at the local level so that the system data base contains no personal identifiers.

The data may be collected by a designated individual or collected by various individuals during the course of the procedure and follow-up data collection. In some exemplary embodiments collection by various individuals may be desirable to facilitate acquiring data in the optimum time frame with respect to performance of the procedure.

As shown in FIG. 2, in step S400, the input data is transmitted to the server. In some exemplary embodiments, it is desirable to strip the data of any confidential identifiers prior to transmission. Further in some embodiments it is preferable to batch data prior to transmission to the server and use a File Transfer Protocol (FTP) to send data to the server.

In an exemplary embodiment the transmission process may begin by establishing a network connection to the server and selecting a software option for transmission, such as an "upload" icon, for example. An upload screen will then appear, with a series of steps. As each step is successfully completed, the next step will appear and the process may be completed by simply following each step in the program. An exemplary upload screen is shown in FIG. 3.

In the exemplary embodiment shown in FIG. 3, the second step verifies that the user's Internet connection is stable and will accommodate a smooth transfer of data. The user may also be asked for a password during this process.

The third step initiates the actual transfer (or upload) of data from the center to the system server. The user may be asked for a password during this process.

The fourth step in completing data transfer in the exemplary embodiment of FIG. 3 is to move all files into the "stock" file. The stock file is the name of the folder where each individual record is stored. This permits later access to individual records or data taken for information only. Such information is typically stored locally (e.g., the user site) to maintain confidentiality yet provide necessary information for follow-up of issues identified in benchmarking. The "stock file" transfer procedure in one embodiment is the archiving of data locally as shown in step S320 of FIG. 2.

Again, referring to FIG. 3, the upload program may be exited upon confirmation of a successful transfer of data as indicated by the software.

Referring again to FIG. 2 in step S500, the system server algorithms compile and analyze input data. Exemplary performance monitoring software is described in detail below. In general, the software has the capacity to convert an outcomes data set to an outcomes result. For example, data for a particular procedure may be selected from data for all procedures; data for a particular indicator for a particular procedure accumulated during a specific time period may be averaged, and the like. Outcomes results may be derived from direct manipulation of input data (e.g., outcomes data set), manipulation of other outcomes results, or any combination thereof.

The performance monitoring software can use multiple outcomes data sets to establish a norm for an outcomes data group. For example, in the case of ambulatory surgery centers, the data from all centers or a selected group of centers may be averaged to determine a norm. Alternatively, a norm for a single center may be established by averaging outcomes data sets for that center taken at designated time intervals, for example.

Benchmarking is achieved by comparing an outcomes result for an indicator or procedure or the like to the norm for that indicator or procedure. As will be apparent in the detailed discussion of the exemplary embodiment of the software of the invention, considerable customization of specific benchmarking is permitted within the system of the invention.

Referring again to FIG. 2, step S600 is the production of the product of the benchmarking process or the feedback report(s) to the user (also referred to herein as outcomes monitoring reports, outcomes reports or reports).

In an Exemplary embodiment reports include benchmarking in which data collected through the system is analyzed to reflect compliance with each of a predetermine number of quality indicators. Although each center has access only to their own data and compliance rates, the reports also may show "average" compliance rates across all participating centers. Individual centers can then compare their rate of compliance against an overall average for a group of centers for each quality indicator or compare an individual center's compliance to that individual center's compliance for another period. Password protection may be used to appropriately restrict access to reports. In one preferred embodiment, Centers may review their reports at any time by accessing a password protected web page. Alternatively reports may be transmitted via e-mail or hard copy means.

Exemplary report types for monitoring produce outcomes for ambulatory surgery procedures may include, for example:

Cumulative Reports: These reports include an accumulation of all data over a specified period of time and will therefore have a large volume/database. These reports may be used for benchmarking a center's averages with averages for all participating centers.

Quarterly Reports: These reports include data for the previous quarter. The quarters are per calendar year, with three months in each quarter. First quarter includes January-March data; second quarter includes April-June; third quarter July-September, and fourth quarter October-December, for example. The primary purpose of the Quarterly Reports to track changes from quarter one quarter to the next.

Current Month Reports: Monthly reports are provided to help identify individual problem cases by including only small portions of data. As a general rule, great care should be taken if using monthly reports for other purposes as the volume of data is often too small to be conclusive of any findings.

Age Distribution is a report that is helpful when information is needed about age prevalence and/or distribution by procedure. All data submitted for each procedure group have been broken down by age, in approximate 10-year increments, for example. This report also gives the average age for that procedure.

Recovery Time shows a breakdown in 30 minute intervals of recovery time for a specific procedure, along with the average recovery time for a center and the average time for all centers.

Surgery Time shows a breakdown in 30 minute intervals of surgery time for a specific procedure, along with the average surgery time for a center and the average time for all centers.

Pain, Complications and Patient Satisfaction is a table showing totals for all data specific to the quality indicators being monitored.

General Indicators shows the rate of compliance to each indicator for a center, and the norm for "all" centers participating in the system. The general indicators report provides a view of a center's outcomes, benchmarked with other centers, at a glance.

Complications by Payor shows a breakdown by payor classification for all complications reported.

Complications by Anesthesia shows a breakdown is by anesthesia type (general, epidural, etc.).

Both newly generated, as well as previous reports, may be accessed by the user.

A report will typically have a defined set of benchmarking indicators. For example indicators in an exemplary embodiment of a benchmarking report for an ambulatory surgery performance outcomes monitoring may include:

Perioperative Indicators
1. Patients experiencing complications of surgery during the perioperative period.
2. Patients retained beyond the expected recovery time for the surgical procedure.
3. Patients returned to surgery.
4. Patients admitted to the hospital following surgery.

5. Patients expressing pain who did not get relief of pain.

Post-Discharge Indicators

6. Patients without significant problems after discharge.
7. Patients expressing pain after discharge who had relief of pain after utilizing pain control methods as instructed.
8. Patients satisfied with preoperative, intraoperative, and postoperative care.
9. Patients who received and understood discharge instructions.
10. Patients adequately prepared for self-care at home after discharge.

Exemplary indicators for an embodiment of the invention for benchmarking ambulatory surgical procedures are described in detail in Example 2 below.

Referring to FIG. 2, in step S800, the user reviews reports. The user, as defined herein, includes all individuals or entities that utilize the benchmarking results. The user may receive a hard copy report or, in preferred embodiments, access the reports via a restricted web page. Each report contains specific results from the user's center (user entity) only or comparisons of the user center's performance to a norm for a group of centers. In an exemplary embodiment, the user is not allowed access to specific reports or specific results for other user centers.

In embodiments utilizing a web page to post results, it is preferable that the web page be restricted or protected such that only an authorized user for a center may access that center's customized report. This may be accomplished through use of known means such as passwords and the like.

In embodiments utilizing a web page for disseminating reports, various features may be included such as a brief definition of each indicator may be shown toward the middle of the report. Further, in an embodiment in which the report is retrieved from a web page, the user may click on the abbreviated wording for a full description of the individual indicator.

User utilization of the reports may, in an exemplary embodiment for ambulatory surgery centers, include the following:

The user may begin by assessing the volume of cases by procedure. As a general rule, at least 30 cases or more are needed before any reports can be considered as statistically significant.

If, for example, data on 866 knee arthroscopies were submitted for a Surgical Center from May 17, 1997-May 31, 1999, this is a considerable volume for this procedure and therefore, the interpretation of reports will have statistical significance. However, if only five (5) cases were submitted for a quarter and one (1) case has complication, the rate of complications will be reflected as 20 percent. As a center continues to report more cases, this percentage may fall considerably. Thus, results based on low volumes may be useful but more antidotal in nature and should not be considered to be statistically significant.

Users have a selection of reports to choose from. In order to make it easier to go from one report to another when viewing the reports from the web page, "links" may be provided to other the benchmarking reports. These links allow the user (when in the on-line mode) to quickly switch from procedure to procedure or from report type to report type. For example, a user can get a quick look at "Surgery Time" for each of their procedures with one click or can also assess all indicators for a given procedure by simply clicking on a link provided on the web page, for example.

An exemplary Quarterly Report showing a comparison of two data sets is provided in FIG. 4. Referring to FIG. 4, the circles reflect a comparison of a center's average to that of the average for all centers. A black circle indicates a center's compliance was "worse than average," a circle with a dot in the middle indicates a center's compliance was within the "average" for all centers, and a white circle indicates compliance rate was "better than the average" reported for all centers.

The arrows reflect changes in compliance rates from the previous quarter (example: fourth quarter rates are compared to third quarter rates, etc.). An arrow pointing downward indicates that the rate this quarter was "worse" than last quarter; arrows going in a straight line indicate no change from last quarter, and arrows pointing upwards indicate the rate has improved from the previous quarter.

Figure 23:
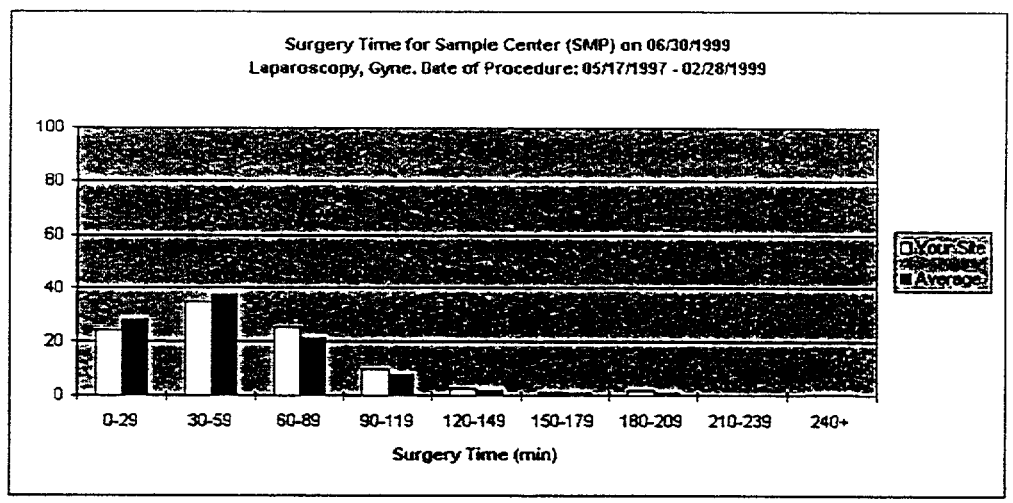
FIG. 23 in an exemplary graphic report in accordance with one embodiment of the invention.

Alternatively, data may be shown in bar graph form including graphic indication of tolerance or statistical variability, or the like. FIGS. 22 and 23 are exemplary of graphic forms of reports.

Software of the Invention

The software of the invention includes software developed for the purpose of analyzing collected outcomes data and preparing reports (collectively the Report System). Among the many features of the Report System software are algorithms that combine data; establish norms; compare data groups; compare data groups to norms; optionally supply statistical data; generate reports from data that is discreetly stored such that various data can be combined to generate a highly customized report in a facile manner; and archive data, combined data and reports both for referral and comparison with data acquired at a later date. The functions of the software are organized in modules. In an exemplary embodiment the modules may include a data-calculation module, data table creator module, chart generator module, comparison table module and report generator module for example. These modules are directed to the tasks of mathematically manipulating data, creating data tables, preparing charts, preparing data comparisons and generating reports, respectively. Each of these modules may have submodules directed to a specific task or type of report. Optionally, additional modules may be included to further address specialized user needs. In the preferred embodiment the reports may be accessed by a user via a restricted web page such as a password protected web page for example and the web page may be suitably equipped with links such that additional reports, other comparisons, explanatory information and the like may be accessed by a simple click, for example.

A flow chart for the structure of one exemplary embodiment of a report system 1000 of the invention is provided in FIG. 5.

As FIG. 5 shows, the structure is subdivided into folders. The folders include among others a database folder 1100, a configuration files folder 1200, a folder for storage of log files 1300, a list folder 1400 containing files related to mathematical calculations and layout of reports, a first templates folder 1500 which stores ready-to-use configuration files for different types of reports, a programs folder 1600 containing all modules of the report system and a second template folder 1700 with files for generating specific report features. We note that exemplary file contents for files of an exemplary embodiment of the invention for monitoring outcomes for ambulatory surgical procedures is provided in Example 1.

As one skilled in the art will recognize the exact composition and number of folder and files may vary considerably within the scope of the invention as the invention is applied to a specific industry or service or as a user group within an industry desires customization. However, the mathematical algorithms used and the general scheme for preparing reports are applicable to the various embodiments of the invention including embodiments for benchmarking performance outcomes in ambulatory surgery, performance outcomes for other medical procedures, service performance outcomes, sales force performance outcomes, manufacturing performance outcomes and the like.

The report system will be described in further detail for one embodiment of the invention for monitoring performance outcomes of ambulatory surgical procedure centers.

Referring to FIG. 5, a first folder is the database folder 1100. This is the main database for the report system. In the exemplary embodiment there are two tables inside this file: MEDREC and PATINT2. MEDREC, contains all medical records and PATINT2 contains all patient interview records. This file is used by the Data_Calculator module (see the description of this module below).

Optionally the folder may also include an archive folder or backup folder or both to store incremental files.

A second folder is the configuration files folder ([INI] folder) 1200. This folder contains the configuration files. These configuration files are designated for an end user and they allow the user to define "what reports will be generated". The files in the exemplary INI folder include Report.ini. This file is used to define the periods to generate reports for. The format of the file may be the following: Name_of_Parameter=Value, for example.

Comments can also be used by typing a ";" character in the beginning of the comment line. Everything after the ";" character may be ignored by the report system performing calculations and analyzing data in the exemplary embodiment. Almost all modules of report system use this file of the type.

An example of the parameters of this exemplary report file may be found in FIG. 6.

Other configuration files may also be included. For example a file (Info file) may be included to provide paths to the different components of the report system. The info file may be used by all modules. An example format of the Info file is: Name_of_Parameter=Value. Exemplary Parameters for an Info file are shown in FIG. 7.

Referring to FIG. 5, a third folder is the Log folder 1300. This folder is used to store log files that are generated by different modules of report system. Files in this folder may include, for example, an Executive_Table.file which is generated by Executive_Table module of the report system; an Executive_Table_Paper_Reports, which is generated by Executive_Table_Paper_Reports module of the report system; a DataTable.file, which is generated by DataTable module of the report system; a Data_Calculator.file, which is generated by Data_Calculator module of the report system; a GrabFile.file, which is generated by GrabFile module of the report system; a ProcDistrib.file, which is generated by ProcDistrib module of the report system; a report.file, which is generated by report module of the report system; and a Comparison_Table.file, which is generated by Comparison_Table module of the report system.

Referring to FIG. 5 a fourth folder is a list folder 1400. This folder contains configuration files like the [INI] folder does. But unlike the [INI] folder, almost all of these files are responsible either for mathematical calculations or for the layout of the reports. Most of these files are a list of strings that have the same structure. Usually each string consists of several fields and the fields are separated by "*" character.

Files in the list folder may include for example an Executive_Table list file, which is used by Executive_Table module. This list file contains a list of indicators that will be shown in a preferred embodiment of a report. The format of each string may be the following:

Indicator_Name*Numerator*Denominator*Description*MinOrMax*Link

Exemplary Executive_table contents are shown in FIG. 8.

An example of parameters associated with this list file is shown in FIG. 4.

Another list file may be a DataTableItems list file. The DataTableItems list file is used by DataTable_Creator module. The DataTable_Creator module generates "Data Tables" file ("DataTable.html"). DataTableItems file may consist of several sections. Each section corresponds to a separate table in "DataTable.html" file. Strings that are located inside each section are used to customize the rows in tables. Each section may begin with one of the following strings:

- - - Name_of_Table*Total_by_Proc_Flag or Name_from_Dump_DB*Row_Name

FIGS. 9 and 10 show examples of the data table items file parameters and associated data tables, respectively.

Another list file may be an Indicators file which is used by the Chart_Generator module. The Indicators file consists of several sections. Each section corresponds to a separate report An exemplary version of Chart_Generator module includes the reports: "Age Distribution," "Recovery Time," "Surgery Time," "General Indicators," "Complications by Payor," "Complication by Anesthesia" for example. Each section may begin with the following string:

- - - With_Tolerance*Without_Tolerance*Chart_Header*Chart_Footer

Example parameters for general report sections are shown in FIG. 11.

Indicators for each section are described after the section header. An example format of indicator description string is the following:

Indicator_Name*Numerator*Denominator*AxesLabels

Figure 13:
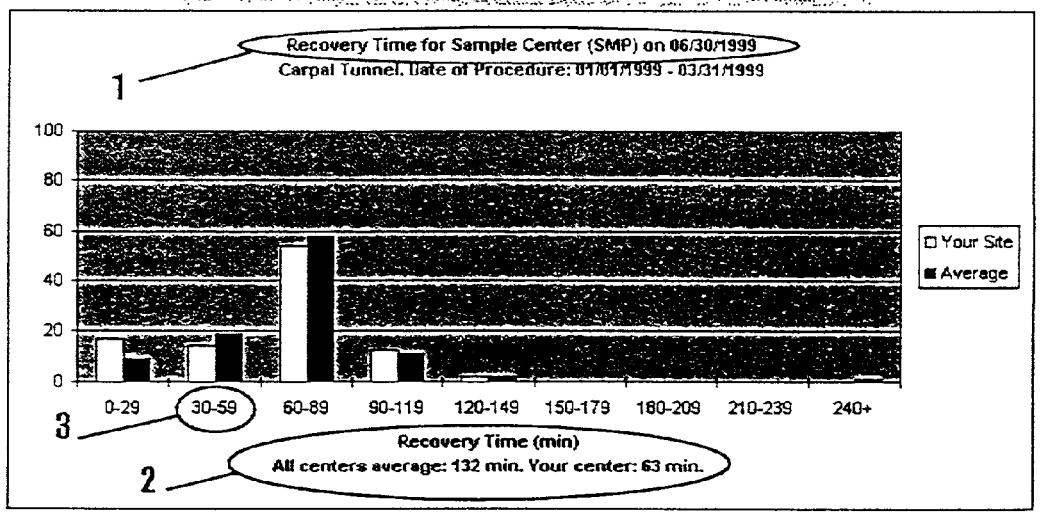
FIG. 13 shows an example of an indicator description report page in accordance with one embodiment of the invention.

FIGS. 12 and 13 show examples of an indicator description string and report page, respectively.

Another list file may be a LogMessages list file which defines different log messages. Most system modules may use this file. The format of each string may be the following:

Message_Name=Text_of_Message where Message_Name is a name of message (report system modules use this name to refer to log messages) and Text_of_Message is a message text. Usually a message text is much longer than Message_Name, so the main purpose of LogMessages list file is to eliminate extra text and also this list file allows similarity of log messages throughout all modules.

Another list file may be a Comparison_table list file which is used by the Comparison_table module. It is divided into several sections. Each section begins with a header and represents a separate group of indicators in "Comparison Table". (This may be used with paper reports, for example). The format of the header is:

- - - Header_of_indicator_group* wherein Header_of_indicator_group contains a text that will be used as a header of the indicator group. If Header_of_indicator_group is empty then no header is used and all indicators in this group have a bold font, for example.

Each section is followed by indicator definitions. The format of these definitions may be the following:

Numerator*Denominator*Descipting_Text*

An example of the parameters of a Comparison table file is found in FIG. 14.

A Corporate_Members list file may be included also. In an exemplary embodiment, this file describes corporate members or unit entities using the benchmarking system. Each unit entity is represented by a separate section. All sections may have a header. The format of headers may be:

- - - GroupName*GroupUsername*GroupUser
Code*members_access where GroupName may be a name of the unit entity; GroupUsername may be a username of the group (this username may be used to access reports); GroupUserCode may be a usercode of the group (a three letter code may be convenient in some embodiments); members_access ("Yes" or "No") may be used to restrict the access of separate members (in individual users) to the reports. members_access may be used by "New_Center_Prepare" module to customize Apache ".htaccess" files for example. Separate members (individual users) of the user entity can access their reports if members_access="Yes" otherwise only GroupUsername can be used to access the reports.

The header of the section may be followed by a list of usercodes of centers that belong to the group. The usercodes may be separated by "Enter" key.

An example of a report of the type which may be presented to a user showing only data for that user and cumulative data for all user groups included in establishing the norm is shown in FIG. 15. Thus, access to a unit entity's individual results may be restricted to that unit entity.

Another file may be a ProcConv list file. This file is used by Appender and Data_Calculator. This file defines a mapping table between the CPT codes and the procedure groups. When Appender module appends new data it ignores the "PROC" fields in incremental files and uses this mapping, in the same way Data_Calculator ignores the existing "PROC" field in the report master database and recreates this field using the mapping. All strings in ProcConv.lst file may have the same format such as:

CPT_Code* Procedure_Group where CPT_Code is a five digit CPT code (procedure code) and Procedure_Group is the name of the corresponding procedure group.

Another list file may be a ProcDistrib file which is used by ProcDistrib module. It defines what fields from "*_dump.mdb" databases should be displayed in the "Case Distribution" table. The format of the file may be the following:

Field_Name*Descripting_Text*

Examples of the file parameter information of a ProcDistrib and a case distribution table are found in FIGS. 16 and 17, respectively. Note that in the example shown in FIG. 17 only two strings are shown TotMR*Medical Records* and TotPI*Patient Interview* this list can be easily expanded.

Another list file may be Sites list file or its equivalent which contains information about centers—it describes relationship between usercodes, real names and usernames. The format of this file may be:

Three_Letter_USERCODE*real_Name_of_center*
Centers_Username where Three_Letter_USERCODE is the usercode of the center; real_Name_of_center is the real name of the center and Centers_Username is the username. Note that string ALL*All centers* MUST be first in some embodiments as this string defines usercode for all centers.

Another list file of the exemplary embodiment is a first Stage list file, (Stage1.lst) which is used by Data_Calculator module only and describes the mathematical expressions using the MS SQL language. To get a table that contains procedure level data for a certain period, Data_Calculator module runs in two stages. On the first stage, the module uses a first stage list file (Stage1.lst) to create a "SELECT"-query that combines MEDREC and PATINT2 tables in one table, for example. Instead of the original fields, this table contains new calculated fields that are used to calculate fields in "*_dump.mdb" files on the next stage. In this stage, the records are not grouped by procedure groups and centers usercodes—they are still patient-level records.

The format of strings of the first stage list file may be the following:

Name_of_Field_1*SQL_Expression

Alternatively a simplified version of "SELECT"-query for use in the first stage may be written in the following way:

SELECT expression_1 AS field_1, ..., expression_k AS field_k, ..., expression_N AS field_N FROM table Name_of_Field is used as field_k and SQL_Expression is used as expression_k.

A second Stage list file (Stage2.lst), which is also used by the Data_Calculator module, describes mathematical expressions using MS SQL language. This file is used on the second stage of the calculation of MasterTable (later, records from MasterTable are used to populate "*_dump.mdb" files). On this stage MasterTable is calculated. It contains procedure-level data. Only this procedure-level data is used by other modules on next the steps of the report generation process.

The format of strings of this file may be the following:

Name_of_Field_2*Data_Type_of_Field*SQL_Expression*Denominator*

Exemplary Stage files are shown in FIGS. 18 and 19.

Referring to FIG. 5, a fifth folder is the first Templates folder 1500. Files in this folder are not used directly by the report system. The purpose of the first templates folder 1500 is to store ready-to-use configuration files for different types of reports. For example, one can use this folder to store configuration files used to generate sample reports. As shown, this folder contains two files only (Sample-Sites.lst and Full_List_Sites.lst)—they are two versions of Sites.lst file: one is for the usual reports, another for sample reports.

Referring again to FIG. 5, a sixth folder is the Programs folder 1600. This folder contains all report modules of the report system. As shown, all modules may be divided into two groups: for "Paper Quarterly Reports" and for "Web Reports". [Paper_Reports] and [Web_Reports] folders were created according to this breakdown.

The [Paper_Reports] subfolder contains modules that are used to generate paper reports. For example, for the "Paper Quarterly Report," HTML files generated by the paper reports modules are created in the folder defined by "SavePathForPaperReport." An exemplary structure of the "Paper_Reports" folder is:

```
[PAPER_REPORTS]
+--- [Comparison_Table]
|     |
|     +--- [Qyyyy-qq]
|           |
|           +---XYZ-FullNameOfXYZ.html
+--- [Executive_Table]
      |
      +--- [Qyyyy-qq]
```

Another exemplary report module is the executive table (Executive_Table_Paper_Reports.exe). This module generates "Executive table" for a paper quarterly report. It may create HTML files for all quarters defined in a report.ini file.

An example of an executive report is shown in FIG. 4.

Another exemplary report module (Comparison_table.exe) generates the "Comparison table" for the paper quarterly report. It may create HTML files for all quarters defined in the "report.ini" file.

A Web_Reports subfolder or its equivalent contains modules of the report system that generate reports to be provided to the user through the Internet or network.

A first file APPENDER or its equivalent may appends incremental files into "Report Master Database" file. It may use only one configuration file. This module may scan all centers directories located under upload directory defined by parameter "UploadDirectory" and append incremental records from these folder to the master database. Appended incremental files are moved to the centers "Backup" folder located under their upload directories.

A second file Chart_Generator or its equivalent may generate the large part of reports for internet dissemination. Chart Generator may, for example, create the following reports in one embodiment:
1. Age Distribution,
2. Recovery Time,
3. Surgery Time,
4. General Indicators,
5. Complications by Payor,
6. Complication by Anesthesia.

This module may use input files including:
1. Corporate Members.lst
2. Indicators.lst
3. "*_dump.mdb", files
4. MasterTable.mdb
5. Sites.lst
6. LogMessages.lst
7. all HTML template files from folder, defined by "TemplateDirectory" parameter in "new-soix.ini"

Reports may be divided into two types: the reports which contain data for all procedure groups in one page and those that have separate page for each procedure group. Report folders for all periods have special sub-folders for each procedure group (in FIG. 20 these folders are shown as [Proc_1], [Proc_2], [Proc_k] and [Proc_Z]) and there are the index files (in FIG. 20 these files are referred as report_index_file_1.html, . . . , report_index_file_M.html) that contain links to this report pages. All these folders and files are generated by the Chart_Generator. Also, this module may refresh main-Old.hmtl, the main page of each center (index.html file that are located directly in the center's folder, not in sub-folders), and index.html files for all recalculated periods.

If a center has a custom picture that is included in "Sites.lst" then its main page and main picture will be updated by Chart_Generator.exe.

In one exemplary embodiment the Chart_Generator.exe module differs from other report modules. When other report modules are running they update only the report files that they generate—they do not delete any other report files, so there is no need to rerun other modules later. When the Chart_Generator module is running, it may delete the whole report folder for a given period.

Other exemplary report modules include an Executive_Table.exe module which creates "The Executive Benchmark Table" tables for web page quarter reports. As input files it uses:
1. Sites.lst
2. Corporate_Members.lst
3. Executive_Table.lst
4. LogMessages.lst
5. "*_dump.mdb" files
6. report.ini
7. new-soix.ini As output files, it creates "Executive_Table.html" files for all quarters defined in "report.ini" file. This module can be easily modified to generate the reports for other periods, in addition to quarters. An exemplary executive table report is shown in FIG. 4.

Another exemplary report module is the DataTable_Creator module which generates indicator results tables such as "Pain, Complication & Patient Satisfaction" tables.

A further exemplary report module may be a Data_Calculator module as its equivalent. This module calculates procedure-level data for all centers. In some exemplary embodiments only this module and "APPENDER" have direct access to the main database, all other modules just use procedure-level data. This serves to eliminate extra calculations, for example if the layout of several reports is changed then there is no need to recalculate the data, one just runs the necessary modules and reports are refreshed. In most cases it takes much less time then when the data should be recalculated.

Another report module may be ProcDistrib_Creator or its equivalent. This module creates "Case Distribution" tables. These tables are created for the whole network. They show case distribution by procedure group and by site inside each procedure group. The number of medical records and patient interviews may be present on these tables in an exemplary embodiment.

Referring to FIG. 5, a seventh folder in one exemplary embodiment is a second Template folder 1700. This folder may contain, for example in an exemplary embodiment, templates for reports such as the "Age Distribution" report used by "Chart_Generator" module; the "Complication by Anesthesia" with tolerance zone report which is used by "Chart_Generator" module; the "Complication by Anesthesia" without tolerance zone report which is used by "Chart_Generator" module; the "General Indicators" with tolerance zone report which is used by "Chart_Generator" module; the "General Indicators" without tolerance zone report which is used by "Chart_Generator" module; the "Reports for Previous Periods" which is used by Chart_Generator module; the loopback file which is shown instead of reports when a center does not have data for certain period and is used by Chart_Generator, DataTable_Creator and ProcDistrib_Creator modules; a main-old file which is used as main page for reports for previous period and contains links to these reports and used by Chart_Generator module; a main-Template file which is used as main index page for "Current Month Reports", "Quarterly Reports" and "Cumulative reports" by the Chart_Generator module; a main.html file which is used as center's main page, includes either default SOIX picture or a favorite picture of the center and is used by Chart_Generator module; a Payor.html file which is a template for "Complications by Payor" reports with tolerance limits and is used by Chart_Generator module; a Payor2.html file which is a template for "Complications by Payor" reports without tolerance limits and used by Chart_Generator module; a RecovTime2.html file which is a template for "Recovery Time" reports and is used by Chart_Generator module; and a SurgTime2.html file which is a template for "Surgery Time" reports and is used by Chart_Generator module.

A subfolder in the template 1700 folder of an exemplary embodiment is an All folder. This folder contains files that are used for reports for the whole network and has the same application as corresponding templates in the first template folder 1500.

Another exemplary subfolder of the templates 1700 folder is an image folder which stores various images that are used for reports. The image folder may contain a centers folder. This folder may be used to store a center's favorite pictures in a format such as "USERCODE. (jpg or gif)", where USERCODE is three-letter user code of a center (For example: aaa.jpg, aza.gif).

Figure 20:
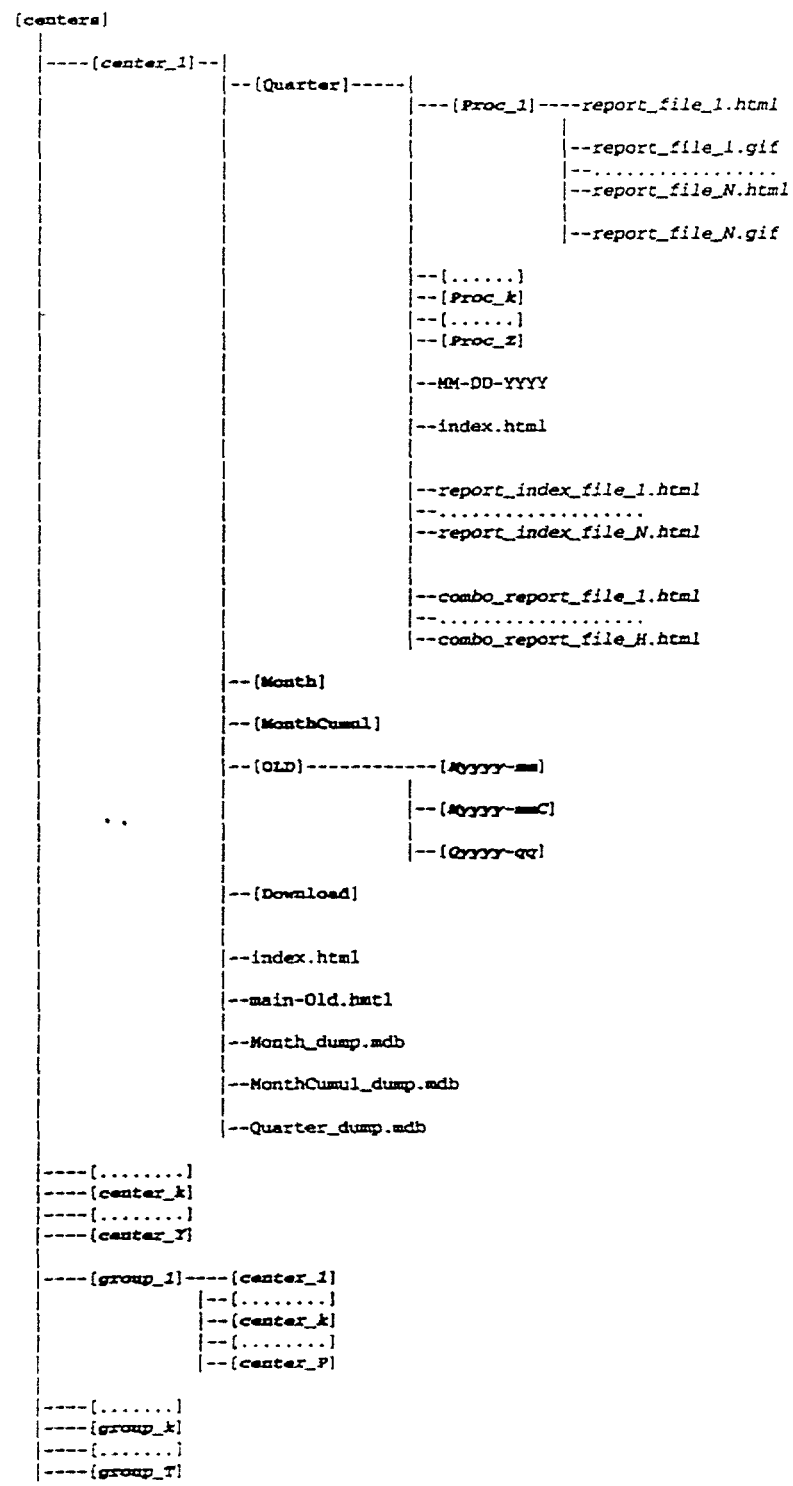
FIG. 20 shows an exemplary report folder structure for a private web site in accordance with one embodiment of the invention.

In a preferred embodiment a user may access the reports prepared via a web page. This web page may be password protected to restrict user access or selectively release specific data to a specified user or both. An exemplary report folder structure for a private web site is shown in FIG. 20.

For this example, folders [center_1], . . . , [center_k], . . . , [center_Y] are the centers report directories corresponding to each center. The name of a center's directory may be a three letter USERCODE of the center for example: AAA, AAB, MFA. Each center has its own home page, for example [center_k]\index.html file.

Each center's folder has file structure which is described below for an exemplary embodiment.

Folders [Month], [Quarter] and [MonthCumul] are used to store "Current Month Report", "Quarterly Reports" and "Cumulative Reports", respectively.

Figure 21:
FIG. 21 is an exemplary menu for accessing previous reports in accordance with one embodiment of the invention.

[OLD] folder is used to store "Reports for the Previous Periods". Each folder inside [OLD] represents reports for a certain period. Folders for quarterly reports have [Qyyyy-qq] names, where "yyyy" is a year in four digit format and "qq" is a quarter number with a leading zero (Example: "Q1999-03"—reports for third quarter of 1999). Files for previous monthly reports are located in [Myyyy-mm] folders, and cumulative monthly reports are saved in [Myyyy-mmC] ones, where "yyyy" is a year and "mm" is a month (Example: "M1999-04"—monthly reports for April 1999, "M1999-03C"—cumulative monthly reports for March 1999). A file shown in FIG. 20 as main-Old.html provides links to reports for the previous periods. An example of a menu that permits a user to use this file is shown in FIG. 21.

Referring again to FIG. 20, a folder such as Download may be used to store center specific files, like "ftprun.run" or updates and patches for OMS program.

Other Database files such as (Month_dump.mdb, MonthCumul_dump.mdb and Quarter_dump.mdb) may contain procedure-level data calculated by the report system. These files store data for "Current Month Reports", "Cumulative Reports" and "Quarterly Reports" respectively. In an exemplary embodiment almost all parts of the report system use these files—not the original Medical Record and Patient Interview patient-level tables.

All report pages may be divided into the two groups:
1) report pages that show information only for a specific procedure group (in current version of the report system these files include a chart and a table corresponding to this chart);
2) report pages that include information for all procedure groups on one page (in current version of the report system these files include tables only).

Index files which do not actually include any reports, may be used to provide access to report pages. Index files may include the following in an exemplary embodiment, for example: an Index file for "Age Distribution" reports; an Index file for "Complication by Anesthesia" reports; an Index file for "General Indicators" reports; an Index file for "Complications by Payor" reports; an Index file for "Recovery Time" reports; and an Index file for "Surgery Time" reports.

Combined files are report files for reports where data for all procedure groups are combined in one file. These files may contain tables only. Examples of such files may include "The Executive Benchmark Table" report table or "Data Tables" report tables, for example.

Another file may be included which is used by the report system to determine the period of reports.

Folders for each procedure group may be included for preparing reports having separate pages for each procedure group. The names of these folders in an exemplary embodiment are derived from the names of corresponding procedure group by skipping all not alphanumeric characters, leaving "_" and "-" symbols in unchanged form and changing all spaces to "_" (For example: the folder for procedure group "D&C/Hysteroscopy" is "DCHysteroscopy", "ENT-T&A<12" is "ENT_-_TA_12"). Each report in these exemplary folders is represented by two files: report_file_k.html and report_file_k.gif. The HTML file includes a table and a chart in GIF format (For example: "Age Distribution" for procedure group "Carpal Tunnel" is represented by the files "Age_Distribution2.html" and "Age Distribution2.gif" in the folder "CarpalTunnel").

In an exemplary embodiment modules may be executed in the following order to create a report: Data_Calculator; Chart_Generator; Executive_Table; DataTable_Creator; and ProcDistrib_Creator.

The order of each module should be completed before moving to the next.

Software will also contain suitable provision for adding and removing user entitles from the benchmarking system.

EXAMPLE 1

The following is a listing of exemplary files contents for data analysis and report preparation for one embodiment of the invention. This example exemplifies one of many groups of files which may be used in ambulatory surgical procedures monitoring and is provided as an illustrative example of the many configuration file types and components which are within the scope of the invention.

Report.ini file

```
;Everything that is located after ";" is comments

[Run options]
CalculationDate  =         ;1/30/2000   ;Date that will be used as creation date in
charts and tables
                                        ;If there is no date then current date is
used MinNumberOfCases =20                ;Minimal number of cases that allows to
generate reports for the procedure group
Confidence       =1.7               ;Coefficient before sigma to calculate
tolerable limits FoundationDate   =1/1/1999

QuarterlyReports =yes       ;Yes or No
QuarterStart     =1         ;1,2,3 or 4
QuarterYearStart =2000      ;format is yyyy
QuarterEnd       =2         ;1,2,3 or 4
QuarterYearEnd   =2000      ;format is yyyy MonthlyReports   =yes       ;Yes or No
MonthStart       =1         ;1 to 12
MonthYearStart   =2000      ;format is yyyy
MonthEnd         =6         ;1 to 12
MonthYearEnd     =2000      ;format is yyyy CumulativeMonthlyReports =yes
CumulativeMonthStart     =1
CumulativeYearStart      =2000
CumulativeMonthEnd       =6
CumulativeYearEnd        =2000

;-----parameters below this line are not supportes at this moment
RunMode          =Auto      ;Auto or Manual CleanedDBF       =no        ;Yes or No
```

```
StandardReport  =no           ;Yes or No
StartDate       =1/1/1998
EndDate         =12/31/1998
```

*Executive_Table.1st* file

```
ind1*Nummer1*TotMR*Perioperative Compli-<br>cations*min*/genrep/ind1.htm
ind2*Nummer2*TotMR*Delayed in Discharge*min*/genrep/ind2.htm
ind3*Nummer3*TotMR*Returns to Surgery*min*/genrep/ind3.htm
ind4*Nummer4*TotMR*Admits to Hospital*min*/genrep/ind4.htm
ind5*Nummer5*Denom5*Pain Episodes Not Relieved<br>*min*/genrep/ind5.htm IND6*Nummer6*TotPI*Care Not Needed After<br> Discharge*max*/genrep/ind6.htm
IND7*Nummer7*Denom7*Pain Controlled After<br> Discharge*max*/genrep/ind7.htm
IND8*Nummer8*TotPI*Satisfied Patients*max*/genrep/ind8.htm
IND9*Nummer9*TotPI*Effective Discharge <br>Instructions*max*/genrep/ind9.htm
IND10*Nummer10*TotPI*Patients Prepared for <br>Self-Care*max*/genrep/ind10.htm
```

*DataTableItems.1st* file

```
---PATIENT DISPOSITION*TotByProc
Patient_Dispos_Normal*Normal
Patient_Dispos_RetainedMore3Hrs*Retained >3 hrs
Patient_Dispos_Hospital*Hospital
Patient_Dispos_Reoperated*Reoperated ---ANESTHESIA*TotByProc
TotEpi*Epidural .
TotGen*General
TotSpi*Spinal
TotMAC*MAC
TotBlock*Block
TotTopical*Topical
TotLoc*Local
TotIVC*IV-CON SED
TotOther*Other
TotNone*None ---PAIN AND COMPLICATIONS*
Pain_Complic_NoPain-NoComplic*No Pain, No<br>Complications
Pain_Complic_Pain*Pain
Pain_Complic_Nausea*Nausea
Pain_Complic_Vomiting*Vomiting
Pain_Complic_InabilityToVoid*Inability To Void
Pain_Complic_Bleeding*Bleeding
Pain_Complic_InstabVitalSigns*Instability Of<br>Vital Signs
Pain_Complic_LevelOfConscChanges*Level Of Conscious-<br>ness Changes
Pain_Complic_RespirProblems*Respiratory<br>Problems
```

---PAIN CONTROL METHODS*
Pain_Control_Meth_PainContrMethExplOnDischarge*Pain
Control<br>Methods Explained<br>on Discharge
Pain_Control_Meth_PrescrGivenOnDischarge*Prescription<br>Given
On Discharge
Pain_Control_Meth_PainVerb*Pain Verbalized
Pain_Control_Meth_MedOrdered*Medication<br>Ordered<br>(Who Had
Pain)
Pain_Control_Meth_MedAdmin*Medication<br>Administered<br>(Who
Had Pain)
Pain_Control_Meth_MedAdminAndRefused*Medication<br>Administere
d<br>And Refused<br>(Who Had Pain)
Pain_Control_Meth_PainRelieved*Pain Relieved<br>(Who Had Pain)

---AFTER LEAVING THE SURGERY CENTER*
After_Leave_Surgery_Problems_Might_Have*Knew What
Problrms<br>Might Have
After_Leave_Surgery_Who_Call*Knew Who To Call
After_Leave_Surgery_Meds_To_Use*Knew What<br>Medicines to Use
After_Leave_Surgery_Had_Appointment*Had an Appointment
After_Leave_Surgery_Had_All_Info*Had All Information ---POSTOPERATIVE PATIENT INTERVIEW:<br>COMPLICATIONS THAT
REQUIRED MEDICAL INTERVENTION*
Postop_Pat_Int_Complic_AnyProblem*Any Problem
Postop_Pat_Int_Complic_Nausea*Nausea
Postop_Pat_Int_Complic_Vomiting*Vomiting
Postop_Pat_Int_Complic_Fever*Fever
Postop_Pat_Int_Complic_ProblemUrine*Problem Urinating
Postop_Pat_Int_Complic_Bleeding*Bleeding
Postop_Pat_Int_Complic_SignsOfInf*Signs Of Infection ---PAIN MANAGEMENT AT HOME*
Pain_Manag_Home_PostopPainAtHome*Postop Pain<br>at Home
Pain_Manag_Home_PostopInstrContrPain*Postop Instructed<br>to
Control Pain<br>at Home
Pain_Manag_Home_ComplWithInstr*Complied with<br>Instructions ---PAIN RELIEF AT HOME FOR PATIENTS WHO HAD PAIN*TotByProc
Pain_Relief_Home_Completely*Completely
Pain_Relief_Home_Greatly*Greatly
Pain_Relief_Home_Somewhat*Somewhat
Pain_Relief_Home_NotRelieved*Not Relieved ---PERCEIVED QUALITY IN REGISTRATION AND ADMISSION
PROCESS*TotByProc

```
Perceived_Quality_Reg_And_Admis_Excellent*Excellent
Perceived_Quality_Reg_And_Admis_Good*Good
Perceived_Quality_Reg_And_Admis_Fair*Fair
Perceived_Quality_Reg_And_Admis_Poor*Poor
Perceived_Quality_Reg_And_Admis_N-A*N/A ---PERCEIVED QUALITY AT PREADMISSION TESTING*TotByProc
Perceived_Quality_Preadmis_Excellent*Excellent
Perceived_Quality_Preadmis_Good*Good
Perceived_Quality_Preadmis_Fair*Fair
Perceived_Quality_Preadmis_Poor*Poor
Perceived_Quality_Preadmis_N-A*N/A ---PERCEIVED QUALITY IN RECOVERY STAGE IN THE CENTER*TotByProc
Perceived_Quality_Rec_Stage_Excellent*Excellent
Perceived_Quality_Rec_Stage_Good*Good
Perceived_Quality_Rec_Stage_Fair*Fair
Perceived_Quality_Rec_Stage_Poor*Poor
Perceived_Quality_Rec_Stage_N-A*N/A
```

*Indicators.1st* file

```
;General Indicators
---ind*ind2*General Indicators*%Average% Records:
%TotMRAllSites%,· %You%: %TotMRThisSite%. %Average%
Interviews: %TotPIAllSites%, %You%: %TotPIThisSite%.
ind1*Nummer1*TotMR*ind1
ind2*Nummer2*TotMR*ind2
ind3*Nummer3*TotMR*ind3
ind4*Nummer4*TotMR*ind4
ind5*Nummer5*Denom5*ind5^^
IND6*Nummer6*TotPI*IND6
IND7*Nummer7*Denom7*IND7^^
IND8*Nummer8*TotPI*IND8
IND9*Nummer9*TotPI*IND9
IND10*Nummer10*TotPI*IND10

;ind1 by payor
---payor*payor2*Complications by Payor*%Average% Average
Complication Rate: %Ind1AllSites%%. %You%: %Ind1ThisSite%%.
Care_Ind1*Care*TotCare*Medicare
Aid_Ind1*Aid*TotAid*Medicaid
Com_Ind1*Com*TotCom*Non-Capitated
Cap_Ind1*Cap*TotCap*Capitated
Uni_Ind1*Uni*TotUni*Uninsured
Wor_Ind1*Wor*TotWor*Workmens Comp
```

```
Oth_Ind1*Oth*TotOth*Other

;ind1 by anesthesia
---anest*anest2*Complications by Anesthesia*%Average%
Average Complication Rate: %Ind1AllSites%%. %You%:
%Ind1ThisSite%%.
EPI_Ind1*EPI*TotEPI*Epidural
GEN_Ind1*GEN*TotGEN*General
Spi_Ind1*Spi*TotSpi*Spinal
MAC_Ind1*MAC*TotMAC*MAC
Block_Ind1*Block*TotBlock*Block
Topical_Ind1*Topical*TotTopical*Topical
Loc_Ind1*Loc*TotLoc*Local
IVC_Ind1*IVC*TotIVC*IV-CON SED
Other_Ind1*Other*TotOther*Other
None_Ind1*None*TotNone*None ;Surgery Time
---*surgtime2*Surgery Time*Surgery Time (min)||%Average%
average: %Surgtime_AvgAllSites% min. %You%:
%Surgtime_AvgThisSite% min.
SURGTIME-0-30V*SURGTIME-0-30*SURGTIME_TOT*0-29
SURGTIME-30-60V*SURGTIME-30-60*SURGTIME_TOT*30-59
SURGTIME-60-90V*SURGTIME-60-90*SURGTIME_TOT*60-89
SURGTIME-90-120V*SURGTIME-90-120*SURGTIME_TOT*90-119
SURGTIME-120-150V*SURGTIME-120-150*SURGTIME_TOT*120-149
SURGTIME-150-180V*SURGTIME-150-180*SURGTIME_TOT*150-179
SURGTIME-180-210V*SURGTIME-180-210*SURGTIME_TOT*180-209
SURGTIME-210-240V*SURGTIME-210-240*SURGTIME_TOT*210-239
SURGTIME-240+V*SURGTIME-240+*SURGTIME_TOT*240+

;Recovery Time
---*recovtime2*Recovery Time*Recovery Time (min)||%Average%
average: %Rectime_AvgAllSites% min. %You%:
%Rectime_AvgThisSite% min.
RECTIME-0-30V*RECTIME-0-30*RECTIME_TOT*0-29
RECTIME-30-60V*RECTIME-30-60*RECTIME_TOT*30-59
RECTIME-60-90V*RECTIME-60-90*RECTIME_TOT*60-89
RECTIME-90-120V*RECTIME-90-120*RECTIME_TOT*90-119
RECTIME-120-150V*RECTIME-120-150*RECTIME_TOT*120-149
RECTIME-150-180V*RECTIME-150-180*RECTIME_TOT*150-179
RECTIME-180-210V*RECTIME-180-210*RECTIME_TOT*180-209
RECTIME-210-240V*RECTIME-210-240*RECTIME_TOT*210-239
RECTIME-240+V*RECTIME-240+*RECTIME_TOT*240+

;Age Distribution
```

```
---*Age_Distribution2*Age Distribution*Age
(years)||%Average% average: %Age_Distrib_AvgAllSites% yrs.
%You%: %Age_Distrib_AvgThisSite% yrs.
Age_Distrib_0-14V*Age_Distrib_0-14*Age_Distrib_Tot*0-14
Age_Distrib_15-24V*Age_Distrib_15-24*Age_Distrib_Tot*15-24
Age_Distrib_25-34V*Age_Distrib_25-34*Age_Distrib_Tot*25-34
Age_Distrib_35-44V*Age_Distrib_35-44*Age_Distrib_Tot*35-44
Age_Distrib_45-54V*Age_Distrib_45-54*Age_Distrib_Tot*45-54
Age_Distrib_55-64V*Age_Distrib_55-64*Age_Distrib_Tot*55-64
Age_Distrib_65-74V*Age_Distrib_65-74*Age_Distrib_Tot*65-74
Age_Distrib_75-84V*Age_Distrib_75-84*Age_Distrib_Tot*75-84
Age_Distrib_85+V*Age_Distrib_85+*Age_Distrib_Tot*85+

---
```

*LogMessages.lst* file

```
ReportStart            = Report Start
ReportEnd              = Report End
KillTreeMsg            = Tree was overwritten or deleted KillFileMsg            = File was overwritten or deleted QuarterReportStart     = Quarter Report is Starting
QuarterReportEnd       = Quarter Report is Completed
MonthReportStart       = Monthly Report is Starting
MonthReportEnd         = Monthly Report is Completed
MonthCumulReportStart  = Cumul Monthly Report is Starting
MonthCumulReportEnd    = Cumul Monthly Report is Completed
StandardReportStart    = Standard Report is Starting
StandardReportEnd      = Standard Report is Completed
```

*Comparison_table.lst* file

```
---*
TotMR*                                         *                              Number of Patients*
---Time (Minutes)*
SurgTime_Avg*                                  *                              Time For Procedure*
RecTime_Avg*                                   *                              Time For Recovery*
IntTime_Avg*                                   *                              Time For Patient Interview*

---Problems Before Leaving Surgery Center*
Patient_Dispos_Normal*                         TotMR*                         Percent Normal Discharge*
Pain_Complic_NoPain-NoComplic*                 TotMR*                         Percent without Problems*
Pain_Control_Meth_PainVerb*                    TotMR*                         Percent with Post Operative
                                                                              Pain*
Pain_Control_Meth_MedOrdered*                  Pain_Control_Meth_PainVerb*       Percent
Medications Ordered*
Pain_Control_Meth_PainRelieved*                Pain_Control_Meth_PainVerb*       Percent Pain
Relieved*
Pain_Control_Meth_PrescrGivenOnDischarge*      TotMR*                         Percent Pain Prescription
Given*
```

```
Pain_Control_Meth_PainContrMethExplOnDischarge*TotMR*        Percent Pain Control Methods
Explained*

---After Leaving the Surgery Center*
After_Leave_Surgery_Problems_Might_Have*   TotPI*            Percent That Knew What
Problems They Might Have*
After_Leave_Surgery_Who_Call*              TotPI*            Percent Knew Who to Call*
After_Leave_Surgery_Meds_To_Use*           TotPI*            Percent Knew Medications to
Control Pain*
After_Leave_Surgery_Had_Appointment*       TotPI*            Percent with Post Operative
Appointment*
After_Leave_Surgery_Had_All_Info*          TotPI*            Percent Who Had Self Care
Info*

---Problems at Home*
Postop_Pat_Int_Complic_AnyProblem*         TotPI*            Percent with Problem Related
to Procedure*
Postop_Pat_Int_Complic_Nausea*             TotPI*               Nausea*
Postop_Pat_Int_Complic_Vomiting*           TotPI*               Vomiting*
Postop_Pat_Int_Complic_Fever*              TotPI*               Fever*
Postop_Pat_Int_Complic_ProblemUrine*       TotPI*               Difficulty
Urinating*
Postop_Pat_Int_Complic_Bleeding*           TotPI*               Bleeding*
Postop_Pat_Int_Complic_SignsOfInf*         TotPI*               Signs of
Infection*
Pain_Manag_Home_PostopPainAtHome*          TotPI*            Percent Bothered by Pain*
Pain_Manag_Home_PostopInstrContrPain*      Pain_Manag_Home_PostopPainAtHome*      Percent with
Instruction about Pain*
Pain_Manag_Home_ComplWithInstr*            Pain_Manag_Home_PostopPainAtHome*      Percent Following
Instructions*
Pain_Relief_Home_Completely*               Pain_Manag_Home_PostopPainAtHome*      Percent
Completely Relieved*

---Perceived Quality of Care*
Nummer8*                                   TotPI*            Percent Excellent Quality*
Perceived_Quality_Reg_And_Admis_Excellent*TotPi*             Percent Excellent
Registration and Admission*
Perceived_Quality_Preadmis_Excellent*      TotPI*            Percent Excellent
Preadmission Testing*
Perceived_Quality_Rec_Stage_Excellent*     TotPI*            Percent Excellent Recovery
Stage*
```

*ProcConv.lst* file

```
29888* Arthroscopic ACL Repair
67916* Blephroplasty
67921* Blephroplasty
19325* Breast augmentation
19120* Breast Biopsy
19318* Breast reduction
31622* Bronchoscopy
31625* Bronchoscopy
28290* Bunionectomy
28292* Bunionectomy
28293* Bunionectomy
28294* Bunionectomy
28296* Bunionectomy
28297* Bunionectomy
28298* Bunionectomy
28299* Bunionectomy
29848* Carpal Tunnel
64721* Carpal Tunnel
66830* Cataract removal
66840* Cataract removal
```

```
66850* Cataract removal
66852* Cataract removal
66920* Cataract removal
66930* Cataract removal
66940* Cataract removal
66983* Cataract removal
66984* Cataract removal
45378* Colonoscopy, diagnostic
45380* Colonoscopy with biopsy
45384* Colonoscopy with biopsy
45385* Colonoscopy with biopsy
52000* Cystoscopy
52005* Cystoscopy
52007* Cystoscopy
52204* Cystoscopy
52281* Cystoscopy
58120* D&C/Hysteroscopy
58558* D&C/Hysteroscopy
43235* EGD
43239* EGD with biopsy
43248* EGD with dilation
43249* EGD with dilation
30520* ENT- Septoplasty
31255* ENT Sinus endoscopy
42820* ENT- T&A < 12
42826* ENT- Tonsillectomy > 12
69436* ENT- Tubes
69631* ENT- Tympanoplasty
49320* GYN laparoscopy
58660* GYN laparoscopy
58670* GYN laparoscopy
58671* GYN laparoscopy
49505* Hernia repair
49585* Hernia repair
29870* Knee Arthroscopy
29877* Knee Arthroscopy
29881* Knee Arthroscopy
29882* Knee Arthroscopy
29884* Knee Arthroscopy
47562* Laparoscopic cholecystectomy
47564* Laparoscopic cholecystectomy
19125* Needle localization breast biopsy
62310* Pain management -epidural
62311* Pain management -epidural
64510* Pain management -epidural
20550* Pain management -injection
55700* Prostate biopsy
```

```
30400*  Rhinoplasty
15828*  Rhytidectomy
23412*  Shoulder Arthroplasty (open)
23450*  Shoulder Arthroplasty (open)
23455*  Shoulder Arthroplasty (open)
29815*  Shoulder Arthroscopy, dx or tx
29819*  Shoulder Arthroscopy, dx or tx
29820*  Shoulder Arthroscopy, dx or tx
29821*  Shoulder Arthroscopy, dx or tx
29822*  Shoulder Arthroscopy, dx or tx
29823*  Shoulder Arthroscopy, dx or tx
29825*  Shoulder Arthroscopy, dx or tx
29826*  Shoulder Arthroscopy, dx or tx 56340*  Laparoscopic cholecystectomy
56342*  Laparoscopic cholecystectomy
56300*  GYN laparoscopy
56302*  GYN laparoscopy
56304*  GYN laparoscopy
56351*  D&C/Hysteroscopy
62275*  Pain management -epidural
62278*  Pain management -epidural
62289*  Pain management -epidural
62298*  Pain management -epidural
```

*Sites.1st* file

```
;"ALL" MUST BE FIRST

ALL*    All Centers*
aaa*    AA Center*                      daniel
aab*    CenterA*                                        helen
aac*    CenterB*                                        debbie
aad*    CenterC*                                jones
aae*    CenterD*                                shannon
aaf*    Z*                              jennifer
```

*Stage1.1st* file

```
;Last Updated: 04/14/2000

DOP*
PAYOR*
DISPOSITIO*
RECTIME*
SURGTIME*
```

```
INTTIME*
AGE*

;Anesthesia*Anesthesia

;----------------------------------------------
;Miscellaneous (PATINT2)
  ;INTTIME2*IIf(TimeDiff([START],[ENDTIME])<0,0,TimeDiff([START],[ENDTIME]))
Disp3*IIf(DISPOSITIO="3",True,False)
Disp2*IIf(DISPOSITIO="2",True,False)

;----------------------------------------------
;Miscellaneous (MEDREC)
Anesthesia3*Left(Anesthesia,3)
PAYOR3*Left(PAYOR,3)
PV*IIf(pv1="Y",True,False)
PR*IIf(pr1="Y",True,False)
Ind2Threshold*

;----------------------------------------------
;General Indicators (PATINT2)
Nummer1_1*IIf(Pain_Complic_Nausea_1 OR Pain_Complic_Vomiting_1 OR Pain_Complic_InabilityToVoid_1 OR
Pain_Complic_Bleeding_1 OR Pain_Complic_InstabVitalSigns_1 OR Pain_Complic_LevelOfConscChanges_1 OR
Pain_Complic_RespirProblems_1,True,False)
Nummer6_1*IIf(Not(IIf(Postop_Pat_Int_Complic_Nausea_1 OR Postop_Pat_Int_Complic_Vomiting_1 OR
Postop_Pat_Int_Complic_Fever_1 OR Postop_Pat_Int_Complic_ProblemUrine_1 OR
Postop_Pat_Int_Complic_Bleeding_1 OR Postop_Pat_Int_Complic_SignsOfInf_1,True,False)) AND
Not(IsNull(PI_IDN)),True,False)
Nummer7_1*IIf((PATINT2.inspain="Y") And Not(Not(folm="Y") and Not(folcom="Y")) And (usem="Y" Or
inscom="Y") And (folm="Y" Or folcom="Y") And (Left(relief,5)="compl") And (phome="Y"),True,False)
Denom7_1*IIf(phome="Y" and Not(Not(folm="Y") and Not(folcom="Y")),True,False)
Nummer8_1*IIf((qregadm="Excellent" OR qregadm="N/A") And (qpreadm="Excellent" OR qpreadm="N/A") And
(qrecov="Excellent" OR qrecov="N/A") AND (NOT (qregadm="N/A" AND qpreadm="N/A" AND
qrecov="N/A")),True,False)
Nummer9_1*IIf(Left(prob,1)="Y" And Left(whocall,1)="Y" And Left(med,1)="Y" And
Left(app,1)="Y",True,False)
Nummer10_1*IIf(Left(inf,1)="Y" And Left(prob,1)="Y" And Left(whocall,1)="Y" And Left(med,1)="Y" And
Left(app,1)="Y",True,False)

;----------------------------------------------
;Pain and Complications (MEDREC)
Pain_Complic_Pain_1*IIf(LEFT(PAIN1,1)="Y" OR LEFT(PAIN2,1)="Y" OR LEFT(PAIN3,1)="Y",True,False)
Pain_Complic_Nausea_1*IIf(LEFT(NAUS1,1)="Y" OR LEFT(NAUS2,1)="Y" OR LEFT(NAUS3,1)="Y",True,False)
Pain_Complic_Vomiting_1*IIf(LEFT(VOM1,1)="Y" OR LEFT(VOM2,1)="Y" OR LEFT(VOM3,1)="Y",True,False)
Pain_Complic_InabilityToVoid_1*IIf(LEFT(INVOID1,1)="Y" OR LEFT(INVOID2,1)="Y" OR
LEFT(INVOID3,1)="Y",True,False)
Pain_Complic_Bleeding_1*IIf(LEFT(MEDREC.BLEED1,1)="Y" OR LEFT(MEDREC.BLEED2,1)="Y" OR
LEFT(MEDREC.BLEED3,1)="Y",True,False)
Pain_Complic_InstabVitalSigns_1*IIf(LEFT(IVS1,1)="Y" OR LEFT(IVS2,1)="Y" OR
LEFT(IVS3,1)="Y",True,False)
Pain_Complic_LevelOfConscChanges_1*IIf(LEFT(LOC1,1)="Y" OR LEFT(LOC2,1)="Y" OR
LEFT(LOC3,1)="Y",True,False)
Pain_Complic_RespirProblems_1*IIf(LEFT(RESP1,1)="Y" OR LEFT(RESP2,1)="Y" OR
LEFT(RESP3,1)="Y",True,False)

;----------------------------------------------
;Pain Control Methods (MEDREC)
Pain_Control_Meth_PrescrGivenOnDischarge_1*IIf(LEFT(PPG,1)="Y" ,True,False)
Pain_Control_Meth_PainContrMethExplOnDischarge_1*IIf(LEFT(PCME,1)="Y" ,True,False)

Pain_Control_Meth_PainVerb_1*IIf(LEFT(PV1,1)="Y",True,False)
Pain_Control_Meth_MedOrdered_1*IIf(LEFT(MO1,1)="Y",True,False) AND Pain_Control_Meth_PainVerb_1
Pain_Control_Meth_MedAdmin_1*IIf(LEFT(MA1,1)="Y",True,False) AND Pain_Control_Meth_PainVerb_1
Pain_Control_Meth_MedAdminAndRefused_1*IIf(LEFT(MA1,1)="R",True,False) AND Pain_Control_Meth_PainVerb_1
Pain_Control_Meth_PainRelieved_1*IIf(LEFT(PR1,1)="Y",True,False) AND Pain_Control_Meth_PainVerb_1

;----------------------------------------------
;After Leaving the Surgery Center (PATINT2)
After_Leave_Surgery_Problems_Might_Have_1*IIf(Left(Prob,1)="Y",True,False)
After_Leave_Surgery_Who_Call_1*IIf(Left(Whocall,1)="Y",True,False)
After_Leave_Surgery_Meds_To_Use_1*IIf(Left(Med,1)="Y",True,False)
After_Leave_Surgery_Had_Appointment_1*IIf(Left(App,1)="Y",True,False)
After_Leave_Surgery_Had_All_Info_1*IIf(Left(Inf,1)="Y",True,False)

;----------------------------------------------
;Postoperative Complications (PATINT2)
Postop_Pat_Int_Complic_Nausea_1*IIf(PATINT2.nausea3="Y" Or PATINT2.nausea4="Y" Or PATINT2.nausea5="Y"
Or PATINT2.nausea6="Y" Or PATINT2.nausea7="Y",True,False)
Postop_Pat_Int_Complic_Vomiting_1*IIf(PATINT2.vomit3="Y" Or PATINT2.vomit4="Y" Or PATINT2.vomit5="Y" Or
PATINT2.vomit6="Y" Or PATINT2.vomit7="Y",True,False)
```

```
Postop_Pat_Int_Complic_Fever_1*IIf(PATINT2.fever3="Y" Or PATINT2.fever4="Y" Or PATINT2.fever5="Y" Or
PATINT2.fever6="Y" Or PATINT2.fever7="Y",True,False)
Postop_Pat_Int_Complic_ProblemUrine_1*IIf(PATINT2.urine3="Y" Or PATINT2.urine4="Y" Or
PATINT2.urine5="Y" Or PATINT2.urine6="Y" Or PATINT2.urine7="Y",True,False)
Postop_Pat_Int_Complic_Bleeding_1*IIf(PATINT2.bleed3="Y" Or PATINT2.bleed4="Y" Or PATINT2.bleed5="Y" Or
PATINT2.bleed6="Y" Or PATINT2.bleed7="Y",True,False)
Postop_Pat_Int_Complic_SignsOfInf_1*IIf(PATINT2.infec3="Y" Or PATINT2.infec4="Y" Or PATINT2.infec5="Y"
Or PATINT2.infec6="Y" Or PATINT2.infec7="Y",True,False)

;-----------------------------------------------
;Postoperative Complications (PATINT2) -- Old Version
;Postop_Pat_Int_Complic_Nausea_1*IIf(Left(Nausea1,1)="Y",True,False)
;Postop_Pat_Int_Complic_Vomiting_1*IIf(Left(Vomit1,1)="Y",True,False)
;Postop_Pat_Int_Complic_Fever_1*IIf(Left(Fever1,1)="Y",True,False)
;Postop_Pat_Int_Complic_ProblemUrine_1*IIf(Left(Urine1,1)="Y",True,False)
;Postop_Pat_Int_Complic_Bleeding_1*IIf(Left(Patint2.Bleed1,1)="Y",True,False)
;Postop_Pat_Int_Complic_SignsOfInf_1*IIf(Left(Infec1,1)="Y",True,False)

;-----------------------------------------------
;Pain Management at Home (PATINT2)
Pain_Manag_Home_PostopPainAtHome_1*IIf(Left(Phome,1)="Y",True,False)
Pain_Manag_Home_PostopInstrContrPain_1*IIf(Left(Phome,1)="Y" AND Left(Inspain,1)="Y",True,False)
Pain_Manag_Home_ComplWithInstr_1*IIf(Left(Phome,1)="Y" AND (Left(Folm,1)="Y" OR Left(Folcom,1)="Y") And
IsNull(Foloth),True,False)

;-----------------------------------------------
;Pain Relief at Home for Patients Who Had Pain (PATINT2)
Pain_Relief_Home_Completely_1*IIf(Left(Phome,1)="Y" AND Left(Relief,3)="Com",True,False)
Pain_Relief_Home_Greatly_1*IIf(Left(Phome,1)="Y" AND Left(Relief,3)="Gre",True,False)
Pain_Relief_Home_Somewhat_1*IIf(Left(Phome,1)="Y" AND Left(Relief,3)="Som",True,False)
Pain_Relief_Home_NotRelieved_1*IIf(Left(Phome,1)="Y" AND Left(Relief,3)="Not",True,False)

;-----------------------------------------------
;Perceived Quality in Registr and Admission Process (PATINT2)
Perceived_Quality_Reg_And_Admis_Excellent_1*IIf(Left(Qregadm,3)="Exc",True,False)
Perceived_Quality_Reg_And_Admis_Good_1*IIf(Left(Qregadm,3)="Goo",True,False)
Perceived_Quality_Reg_And_Admis_Fair_1*IIf(Left(Qregadm,3)="Fai",True,False)
Perceived_Quality_Reg_And_Admis_Poor_1*IIf(Left(Qregadm,3)="Poo",True,False)
Perceived_Quality_Reg_And_Admis_N-A_1*IIf(Left(Qregadm,3)="N/A",True,False)

;-----------------------------------------------
;Perceived Quality at Preadmission Testing (PATINT2)
Perceived_Quality_Preadmis_Excellent_1*IIf(Left(Qpreadm,3)="Exc",True,False)
Perceived_Quality_Preadmis_Good_1*IIf(Left(Qpreadm,3)="Goo",True,False)
Perceived_Quality_Preadmis_Fair_1*IIf(Left(Qpreadm,3)="Fai",True,False)
Perceived_Quality_Preadmis_Poor_1*IIf(Left(Qpreadm,3)="Poo",True,False)
Perceived_Quality_Preadmis_N-A_1*IIf(Left(Qpreadm,3)="N/A",True,False)

;-----------------------------------------------
;Perceived Quality in Recovery stage in the Center (PATINT2)
Perceived_Quality_Rec_Stage_Excellent_1*IIf(Left(Qrecov,3)="Exc",True,False)
Perceived_Quality_Rec_Stage_Good_1*IIf(Left(Qrecov,3)="Goo",True,False)
Perceived_Quality_Rec_Stage_Fair_1*IIf(Left(Qrecov,3)="Fai",True,False)
Perceived_Quality_Rec_Stage_Poor_1*IIf(Left(Qrecov,3)="Poo",True,False)
Perceived_Quality_Rec_Stage_N-A_1*IIf(Left(Qrecov,3)="N/A",True,False)

;-----------------------------------------------
;Age Distribution (MEDREC)
Age_Distrib_0-14_1*IIf(AGE>0 AND AGE<15,True,False)
Age_Distrib_15-24_1*IIf(AGE>=15 AND AGE<25,True,False)
Age_Distrib_25-34_1*IIf(AGE>=25 AND AGE<35,True,False)
Age_Distrib_35-44_1*IIf(AGE>=35 AND AGE<45,True,False)
Age_Distrib_45-54_1*IIf(AGE>=45 AND AGE<55,True,False)
Age_Distrib_55-64_1*IIf(AGE>=55 AND AGE<65,True,False)
Age_Distrib_65-74_1*IIf(AGE>=65 AND AGE<75,True,False)
Age_Distrib_75-84_1*IIf(AGE>=75 AND AGE<85,True,False)
Age_Distrib_85+_1*IIf(AGE>=85 AND AGE<=120,True,False)
Age_Distrib_Tot_1*IIf(AGE>0 AND AGE<=120,True,False)

;-----------------------------------------------
;Recovery Time Distrubution (MEDREC)
RECTIME-0-30_1*IIf(RECTIME>0 and RECTIME<30,True,False)
RECTIME-30-60_1*IIf(RECTIME>=30 and RECTIME<60,True,False)
RECTIME-60-90_1*IIf(RECTIME>=60 and RECTIME<90,True,False)
RECTIME-90-120_1*IIf(RECTIME>=90 and RECTIME<120,True,False)
RECTIME-120-150_1*IIf(RECTIME>=120 and RECTIME<150,True,False)
RECTIME-150-180_1*IIf(RECTIME>=150 and RECTIME<180,True,False)
RECTIME-180-210_1*IIf(RECTIME>=180 and RECTIME<210,True,False)
RECTIME-210-240_1*IIf(RECTIME>=210 and RECTIME<240,True,False)
RECTIME-240+_1*IIf(RECTIME>=240 ,True,False)
RECTIME_TOT_1*IIf(RECTIME>0 ,True,False)
```

```
;----------------------------------------------------------
;Surgery Time Distribution (MEDREC)
SURGTIME-0-30_1*IIf(SURGTIME>0 and SURGTIME<30,True,False)
SURGTIME-30-60_1*IIf(SURGTIME>=30 and SURGTIME<60,True,False)
SURGTIME-60-90_1*IIf(SURGTIME>=60 and SURGTIME<90,True,False)
SURGTIME-90-120_1*IIf(SURGTIME>=90 and SURGTIME<120,True,False)
SURGTIME-120-150_1*IIf(SURGTIME>=120 and SURGTIME<150,True,False)
SURGTIME-150-180_1*IIf(SURGTIME>=150 and SURGTIME<180,True,False)
SURGTIME-180-210_1*IIf(SURGTIME>=180 and SURGTIME<210,True,False)
SURGTIME-210-240_1*IIf(SURGTIME>=210 and SURGTIME<240,True,False)
SURGTIME-240+_1*IIf(SURGTIME>=240 ,True,False)
SURGTIME_TOT_1*IIf(SURGTIME>0 ,True,False)
```

*Stage2.lst* file

```
;----------------------------------------------------------
;Header
TotMR*              Long*           Count(Site)**
TotPI*              Long*           Count(PI_IDN)**

;----------------------------------------------------------
;General Indicators (MEDREC)
Nummer1*            Long*           Count(IIf(Nummer1_1,True,Null))**
Nummer2*            Long*           Count(IIf(RECTIME>Ind2Threshold,True,Null))**
Nummer3*            Long*           Count(IIf(Disp3,True,Null))**
Nummer4*            Long*           Count(IIf(Disp2,True,Null))**
Nummer5*            Long*           Count(IIf(PV And Not(PR),True,Null))**
Denom5*             Long*           Count(IIf(PV,True,Null))**

;----------------------------------------------------------
;General Indicators (PATINT2)
Nummer6*            Long*           Count(IIf(Nummer6_1,True,Null))**
Nummer7*            Long*           Count(IIf(Nummer7_1,True,Null))**
Denom7*             Long*           Count(IIf(Denom7_1,True,Null))**
Nummer8*            Long*           Count(IIf(Nummer8_1,True,Null))**
Nummer9*            Long*           Count(IIf(Nummer9_1,True,Null))**
Nummer10*           Long*           Count(IIf(Nummer10_1,True,Null))**

;----------------------------------------------------------
;Complications by Payor (MEDREC)
TotCare*            Long*           Count(IIf(PAYOR="Medicare",True,Null))**
Care*               Long*           Count(IIf(PAYOR="Medicare" AND Nummer1_1,True,Null))**
TotAid*             Long*           Count(IIf(PAYOR="Medicaid",True,Null))**
Aid*                Long*           Count(IIf(PAYOR="Medicaid" AND Nummer1_1,True,Null))**
TotCom*             Long*           Count(IIf(Payor3="Com",True,Null))**
Com*                Long*           Count(IIf(Payor3="Com" AND Nummer1_1,True,Null))**
TotCap*             Long*           Count(IIf(Payor3="Cap",True,Null))**
Cap*                Long*           Count(IIf(Payor3="Cap" AND Nummer1_1,True,Null))**
TotUni*             Long*           Count(IIf(Payor3="Uni",True,Null))**
Uni*                Long*           Count(IIf(Payor3="Uni" AND Nummer1_1,True,Null))**
TotWor*             Long*           Count(IIf(Payor3="Wor",True,Null))**
Wor*                Long*           Count(IIf(Payor3="Wor" AND Nummer1_1,True,Null))**
TotOth*             Long*           Count(IIf(Payor3="Oth",True,Null))**
Oth*                Long*           Count(IIf(Payor3="Oth" AND Nummer1_1,True,Null))**

;----------------------------------------------------------
;Complications by Anesthesia (MEDREC)
TotEpi*             Long*           Count(IIf(Anesthesia3="Epi",True,Null))**
Epi*                Long*           Count(IIf(Anesthesia3="Epi" AND Nummer1_1,True,Null))**
TotGen*             Long*           Count(IIf(Anesthesia3="Gen",True,Null))**
Gen*                Long*           Count(IIf(Anesthesia3="Gen" AND Nummer1_1,True,Null))**
TotSpi*             Long*           Count(IIf(Anesthesia3="Spi",True,Null))**
Spi*                Long*           Count(IIf(Anesthesia3="Spi" AND Nummer1_1,True,Null))**
TotMAC*             Long*           Count(IIf(Anesthesia3="MAC",True,Null))**
MAC*                Long*           Count(IIf(Anesthesia3="MAC" AND Nummer1_1,True,Null))**
TotBlock*           Long*           Count(IIf(Anesthesia3="Blo",True,Null))**
Block*              Long*           Count(IIf(Anesthesia3="Blo" AND Nummer1_1,True,Null))**
TotTopical*         Long*           Count(IIf(Anesthesia3="Top",True,Null))**
Topical*            Long*           Count(IIf(Anesthesia3="Top" AND Nummer1_1,True,Null))**
TotLoc*             Long*           Count(IIf(Anesthesia3="Loc",True,Null))**
Loc*                Long*           Count(IIf(Anesthesia3="Loc" AND Nummer1_1,True,Null))**
TotIVC*             Long*           Count(IIf(Anesthesia3="IV-",True,Null))**
IVC*                Long*           Count(IIf(Anesthesia3="IV-" AND Nummer1_1,True,Null))**
TotOther*           Long*           Count(IIf(Anesthesia3="Oth",True,Null))**
Other*              Long*           Count(IIf(Anesthesia3="Oth" AND Nummer1_1,True,Null))**
TotNone*            Long*           Count(IIf(Anesthesia3="Non",True,Null))**
None*               Long*           Count(IIf(Anesthesia3="Non" AND Nummer1_1,True,Null))**
```

```
;-------------------------------------------------
;Pain Disposition (MEDREC)
Patient_Dispos_RetainedMore3Hrs*    Long*       Count(IIf(DISPOSITIO="1",True,Null))**
Patient_Dispos_Hospital*            Long*       Count(IIf(DISPOSITIO="2",True,Null))**
Patient_Dispos_Reoperated*          Long*       Count(IIf(DISPOSITIO="3",True,Null))**
Patient_Dispos_Normal*              Long*       Count(IIf(DISPOSITIO="4",True,Null))**

;-------------------------------------------------
;Pain and Complications (MEDREC)
Pain_Complic_NoPain-NoComplic*          Long*       Count(IIf(Pain_Complic_Pain_1 OR Pain_Complic_Nausea_1
OR Pain_Complic_Vomiting_1 OR Pain_Complic_InabilityToVoid_1 OR Pain_Complic_Bleeding_1 OR
Pain_Complic_InstabVitalSigns_1 OR Pain_Complic_LevelOfConscChanges_1 OR
Pain_Complic_RespirProblems_1,Null,True))**
Pain_Complic_Pain*                  Long*       Count(IIf(Pain_Complic_Pain_1,True,Null))**
Pain_Complic_Nausea*                Long*       Count(IIf(Pain_Complic_Nausea_1,True,Null))**
Pain_Complic_Vomiting*              Long*       Count(IIf(Pain_Complic_Vomiting_1,True,Null))**
Pain_Complic_InabilityToVoid*       Long*       Count(IIf(Pain_Complic_InabilityToVoid_1,True,Null))**
Pain_Complic_Bleeding*              Long*       Count(IIf(Pain_Complic_Bleeding_1,True,Null))**
Pain_Complic_InstabVitalSigns*      Long*       Count(IIf(Pain_Complic_InstabVitalSigns_1,True,Null))**
Pain_Complic_LevelOfConscChanges*   Long*
Count(IIf(Pain_Complic_LevelOfConscChanges_1,True,Null))**
Pain_Complic_RespirProblems*        Long*       Count(IIf(Pain_Complic_RespirProblems_1,True,Null))**

;-------------------------------------------------
;Pain Control Methods (MEDREC)
Pain_Control_Meth_PainVerb*                     Long*
Count(IIf(Pain_Control_Meth_PainVerb_1,True,Null))**
Pain_Control_Meth_MedOrdered*                   Long*
Count(IIf(Pain_Control_Meth_MedOrdered_1,True,Null))**
Pain_Control_Meth_MedAdmin*                     Long*
Count(IIf(Pain_Control_Meth_MedAdmin_1,True,Null))**
Pain_Control_Meth_MedAdminAndRefused*           Long*
Count(IIf(Pain_Control_Meth_MedAdminAndRefused_1,True,Null))**
Pain_Control_Meth_PainRelieved*                 Long*
Count(IIf(Pain_Control_Meth_PainRelieved_1,True,Null))**
Pain_Control_Meth_PrescrGivenOnDischarge*       Long*
Count(IIf(Pain_Control_Meth_PrescrGivenOnDischarge_1,True,Null))**
Pain_Control_Meth_PainContrMethExplOnDischarge* Long*
Count(IIf(Pain_Control_Meth_PainContrMethExplOnDischarge_1,True,Null))**

;-------------------------------------------------
;After Leaving the Surgery Center (PATINT2)
After_Leave_Surgery_Problems_Might_Have*        Long*
Count(IIf(After_Leave_Surgery_Problems_Might_Have_1,True,Null))**
After_Leave_Surgery_Who_Call*                   Long*
Count(IIf(After_Leave_Surgery_Who_Call_1,True,Null))**
After_Leave_Surgery_Meds_To_Use*                Long*
Count(IIf(After_Leave_Surgery_Meds_To_Use_1,True,Null))**
After_Leave_Surgery_Had_Appointment*            Long*
Count(IIf(After_Leave_Surgery_Had_Appointment_1,True,Null))**
After_Leave_Surgery_Had_All_Info*               Long*
Count(IIf(After_Leave_Surgery_Had_All_Info_1,True,Null))**

;-------------------------------------------------
;Postoperative Complications (PATINT2)
Postop_Pat_Int_Complic_AnyProblem*      Long*       Count(IIf(Postop_Pat_Int_Complic_Nausea_1 OR
Postop_Pat_Int_Complic_Vomiting_1 OR Postop_Pat_Int_Complic_Fever_1 OR Postop_Pat_Int_Complic_ProblemUrine_1
OR Postop_Pat_Int_Complic_Bleeding_1 OR Postop_Pat_Int_Complic_SignsOfInf_1,True,Null))**

Postop_Pat_Int_Complic_Nausea*                  Long*
Count(IIf(Postop_Pat_Int_Complic_Nausea_1,True,Null))**
Postop_Pat_Int_Complic_Vomiting*                Long*
Count(IIf(Postop_Pat_Int_Complic_Vomiting_1,True,Null))**
Postop_Pat_Int_Complic_Fever*                   Long*
Count(IIf(Postop_Pat_Int_Complic_Fever_1,True,Null))**
Postop_Pat_Int_Complic_ProblemUrine*            Long*
Count(IIf(Postop_Pat_Int_Complic_ProblemUrine_1,True,Null))**
Postop_Pat_Int_Complic_Bleeding*                Long*
Count(IIf(Postop_Pat_Int_Complic_Bleeding_1,True,Null))**
Postop_Pat_Int_Complic_SignsOfInf*              Long*
Count(IIf(Postop_Pat_Int_Complic_SignsOfInf_1,True,Null))**

;-------------------------------------------------
;Pain Management at Home (PATINT2)
Pain_Manag_Home_PostopPainAtHome*               Long*
Count(IIf(Pain_Manag_Home_PostopPainAtHome_1,True,Null))**
Pain_Manag_Home_PostopInstrContrPain*           Long*
Count(IIf(Pain_Manag_Home_PostopInstrContrPain_1,True,Null))**
```

```
· Pain_Manag_Home_ComplWithInstr*          Long*
Count(IIf(Pain_Manag_Home_ComplWithInstr_1,True,Null))**

;--------------------------------------------
;Pain Relief at Home for Patients Who Had Pain (PATINT2)
Pain_Relief_Home_Completely*        Long*        Count(IIf(Pain_Relief_Home_Completely_1,True,Null))**
Pain_Relief_Home_Greatly*           Long*        Count(IIf(Pain_Relief_Home_Greatly_1,True,Null))**
Pain_Relief_Home_Somewhat*          Long*        Count(IIf(Pain_Relief_Home_Somewhat_1,True,Null))**
Pain_Relief_Home_NotRelieved*       Long*        Count(IIf(Pain_Relief_Home_NotRelieved_1,True,Null))**

;--------------------------------------------
;Perceived Quality in Registr and Admission Process (PATINT2)
Perceived_Quality_Reg_And_Admis_Excellent*          Long*
Count(IIf(Perceived_Quality_Reg_And_Admis_Excellent_1,True,Null))**
Perceived_Quality_Reg_And_Admis_Good*               Long*
Count(IIf(Perceived_Quality_Reg_And_Admis_Good_1,True,Null))**
Perceived_Quality_Reg_And_Admis_Fair*               Long*
Count(IIf(Perceived_Quality_Reg_And_Admis_Fair_1,True,Null))**
Perceived_Quality_Reg_And_Admis_Poor*               Long*
Count(IIf(Perceived_Quality_Reg_And_Admis_Poor_1,True,Null))**
Perceived_Quality_Reg_And_Admis_N-A*                Long*        Count(IIf([Perceived_Quality_Reg_And_Admis_N-
A_1],True,Null))**

;--------------------------------------------
;Perceived Quality at Preadmission Testing (PATINT2)
Perceived_Quality_Preadmis_Excellent*       Long*
Count(IIf(Perceived_Quality_Preadmis_Excellent_1,True,Null))**
Perceived_Quality_Preadmis_Good*            Long*
Count(IIf(Perceived_Quality_Preadmis_Good_1,True,Null))**
Perceived_Quality_Preadmis_Fair*            Long*
Count(IIf(Perceived_Quality_Preadmis_Fair_1,True,Null))**
Perceived_Quality_Preadmis_Poor*            Long*
Count(IIf(Perceived_Quality_Preadmis_Poor_1,True,Null))**
Perceived_Quality_Preadmis_N-A*             Long*        Count(IIf([Perceived_Quality_Preadmis_N-
A_1],True,Null))**

;--------------------------------------------
;Perceived Quality in Recovery stage in the Center (PATINT2)
Perceived_Quality_Rec_Stage_Excellent*      Long*
Count(IIf(Perceived_Quality_Rec_Stage_Excellent_1,True,Null))**
Perceived_Quality_Rec_Stage_Good*           Long*
Count(IIf(Perceived_Quality_Rec_Stage_Good_1,True,Null))**
Perceived_Quality_Rec_Stage_Fair*           Long*
Count(IIf(Perceived_Quality_Rec_Stage_Fair_1,True,Null))**
Perceived_Quality_Rec_Stage_Poor*           Long*
Count(IIf(Perceived_Quality_Rec_Stage_Poor_1,True,Null))**
Perceived_Quality_Rec_Stage_N-A*            Long*        Count(IIf([Perceived_Quality_Rec_Stage_N-
A_1],True,Null))**

;--------------------------------------------
;Age distribution (MEDREC)
Age_Distrib_Avg*        Single*     Avg(IIf(AGE>0 AND AGE<120,AGE,Null))*       Age_Distrib_Tot*
Age_Distrib_0-14*       Long*       Count(IIf([Age_Distrib_0-14_1],True,Null))**
Age_Distrib_15-24*      Long*       Count(IIf([Age_Distrib_15-24_1],True,Null))**
Age_Distrib_25-34*      Long*       Count(IIf([Age_Distrib_25-34_1],True,Null))**
Age_Distrib_35-44*      Long*       Count(IIf([Age_Distrib_35-44_1],True,Null))**
Age_Distrib_45-54*      Long*       Count(IIf([Age_Distrib_45-54_1],True,Null))**
Age_Distrib_55-64*      Long*       Count(IIf([Age_Distrib_55-64_1],True,Null))**
Age_Distrib_65-74*      Long*       Count(IIf([Age_Distrib_65-74_1],True,Null))**
Age_Distrib_75-84*      Long*       Count(IIf([Age_Distrib_75-84_1],True,Null))**
Age_Distrib_85+*        Long*       Count(IIf([Age_Distrib_85+_1],True,Null))**
Age_Distrib_Tot*        Long*       Count(IIf([Age_Distrib_Tot_1],True,Null))**

;--------------------------------------------
;Recovery Time Distrubution (MEDREC)
Rectime_Avg*            Single*     Avg(RECTIME)*                               RECTIME_TOT*
RECTIME-0-30*           Long*       Count(IIf([RECTIME-0-30_1],True,Null))**
RECTIME-30-60*          Long*       Count(IIf([RECTIME-30-60_1],True,Null))**
RECTIME-60-90*          Long*       Count(IIf([RECTIME-60-90_1],True,Null))**
RECTIME-90-120*         Long*       Count(IIf([RECTIME-90-120_1],True,Null))**
RECTIME-120-150*        Long*       Count(IIf([RECTIME-120-150_1],True,Null))**
RECTIME-150-180*        Long*       Count(IIf([RECTIME-150-180_1],True,Null))**
RECTIME-180-210*        Long*       Count(IIf([RECTIME-180-210_1],True,Null))**
RECTIME-210-240*        Long*       Count(IIf([RECTIME-210-240_1],True,Null))**
RECTIME-240+*           Long*       Count(IIf([RECTIME-240+_1],True,Null))**
RECTIME_TOT*            Long*       Count(IIf([RECTIME_TOT_1],True,Null))**

;--------------------------------------------
;Surgery Time Distribution (MEDREC)
Surgtime_Avg*           Single*     Avg(SURGTIME)*                              SURGTIME_TOT*
SURGTIME-0-30*          Long*       Count(IIf([SURGTIME-0-30_1],True,Null))**
```

```
SURGTIME-30-60*         Long*      Count(IIf(([SURGTIME-30-60_1],True,Null))**
SURGTIME-60-90*         Long*      Count(IIf(([SURGTIME-60-90_1],True,Null))**
SURGTIME-90-120*        Long*      Count(IIf(([SURGTIME-90-120_1],True,Null))**
SURGTIME-120-150*       Long*      Count(IIf(([SURGTIME-120-150_1],True,Null))**
SURGTIME-150-180*       Long*      Count(IIf(([SURGTIME-150-180_1],True,Null))**
SURGTIME-180-210*       Long*      Count(IIf(([SURGTIME-180-210_1],True,Null))**
SURGTIME-210-240*       Long*      Count(IIf(([SURGTIME-210-240_1],True,Null))**
SURGTIME-240+*          Long*      Count(IIf(([SURGTIME-240+_1],True,Null))**
SURGTIME_TOT*           Long*      Count(IIf(([SURGTIME_TOT_1],True,Null))**

;--------------------------------------------------
;Miscellaneous (PATINT2)
IntTime_Avg*            Single*    Avg(IIf(INTTIME>=1 AND INTTIME<=20,INTTIME,Null))*      TotPI*
```

Corporate_Members.1st file

```
;Format:
;
;---Group's Name*Group's Username* Group's UserCode*Allow
separate members to access their reports (Yes|No)
;center1
;center2

---ASC Group*pinewood*zaa*no
aba
abh
acd
acc
abi
abj
abg
abk
``` new-soix.ini file

```
;This file includes paths to Program folder, INI folder and
Log folder.
;Edit it and copy to %windir% directory
;Caution: Do not put "\" at the end of folder names ;----------Shared parameters
INIPath
=c:\SOIX\Soix_Report_System\INI
LogPath
=c:\SOIX\Soix_Report_System\Log OMS2ArchiveDirectory
=c:\SOIX\Soix_Report_System\DATA\OMS2_Archive
```

```
OMS2BackupDirectory
=c:\SOIX\Soix_Report_System\DATA\OMS2_Backup

MDBFile
=c:\SOIX\Soix_Report_System\DATA\SOIX.MDB
LSTPath
=c:\SOIX\Soix_Report_System\lst
TemplateDirectory
=c:\SOIX\Soix_Report_System\TEMPLATE
UploadDirectory
=C:\SOIX\WebSites\SOIX\upload
InternetDirectory
=C:\SOIX\WebSites\SOIX\Centers
NewReportsInternetDirectory     =C:\SOIX\WebSites\SOIX\NEW ;----------for paper reports
SavePathForPaperReport
=c:\SOIX\WebSites\SOIX\Paper_Reports
;Target = Web | Folder
Target                          =Folder ;----------New sites preparation
NTSecDirectory                  =c:\Admin_Stuff\NTSec
ApacheUsersFile                 =C:\SOIX\WebSites\soix_users
ApacheGroupsFile
=C:\SOIX\WebSites\soix_groups
NewCenterTemplateFolder
=c:\SOIX\Soix_Report_System\Template\NewCenterTemplateFolder
PrepareUploadStuff              =Yes
PrepareDownloadStuff            =Yes
PrepareHTMLFiles                =Yes
```

EXAMPLE 2

Exemplary indicators for benchmarking ambulatory surgical procedures in one exemplary embodiment of the invention include the following:

Indicator 1

General Criteria: Patients experiencing complications of surgery during the perioperative period.

Indicator Logic And Calculation Concepts

Definition

The percent of all patients experiencing one or more of the following complications during the intraoperative or postoperative period while in the center:

Nausea
Vomiting
Instability of vital signs
Respiratory problems
Level of consciousness changes
Hemorrhage/bleeding
Inability to void requiring catheterization (excludes intraoperative catheterization)

This indicator may be reported by the payor, the procedure, and the anesthesia method Type of Indicator This is a rate-based indicator of operative complications addressing a process of care with an optimal value of zero. This indicator is stated in terms of a negative outcome; therefore, higher rates should be viewed as opportunities for further review and improvement. Lower rates are generally considered better outcomes.

Rationale

Development of operative and postoperative complications may or may not suggest a quality problem. Complications add additional cost to the treatment of patients and/or increase patient risk, length of stay, and recovery time.

Calculation Concepts

Numerator=Total Number of Patients Experiencing Complications

Denominator=Total Number of Ambulatory Surgical Patients

Indicator Rate=(Numerator/Denominator)*100

Data Source

Medical Record Abstract Form:

A response under the column for intra or post-operative PROBLEMS for any of the following: nausea, vomiting, inability to void, hemorrhage/bleeding, instability of vital signs, respiratory problems, or LOC changes, will be counted as meeting criteria 1, Patients experiencing complications of surgery during the perioperative period.

Indicator 2

Patients retained beyond the expected recovery time for the surgical procedure.

Indicator Logic And Calculation Concepts

Definition

Percent of all patients who remained in the recovery area(s) beyond the expected recovery time.

Recovery time is defined as the period of time between the time at which the procedure is completed and the time at which the patient meets discharge criteria. (If the time at which the patient met discharge criteria is not documented, the recovery time is calculated as the period of time between the time at which the procedure is completed and the discharge time). A patient's recovery time is considered to be longer than expected if it exceeds the two sigma deviation for all patients undergoing the same procedure.

Type of Indicator

This is a rate-based indicator addressing a process and outcome of care with an optimal value of zero.

This indicator is stated in terms of a negative outcome; therefore, higher rates should be viewed as opportunities for further review and improvement. Lower rates are generally considered better outcomes.

Rationale

Retention of patients beyond the expected recovery time may or may not suggest a quality problem. Retention adds additional cost to the treatment of patients and subjects a patient to inconvenience or unexpected hardships associated with an extended length of stay or a prolonged recovery period.

Calculation Concepts

Numerator=Total Number of Patients Retained Beyond Expected Recovery Time

Denominator=Total Number of Ambulatory Surgical Patients

Indicator Rate=(Numerator / Denominator)*100

Data Source

Medical Record Abstract Form; procedure information

Indicator 3

Patients returned to surgery.

Indicator Logic And Calculation Concepts

Definitions

Percent of all patients who were returned to surgery at any time during the postoperative period in the ambulatory surgery center.

Type of Indicator

This is a rate-based indicator of total returns to surgery within the current postoperative period addressing an outcome of care with an optimal value of zero.

This indicator is stated in terms of a negative outcome; therefore, higher rates should be viewed as opportunities for further review and improvement. Lower rates are generally considered better outcomes.

Rationale

An additional surgical procedure during the current surgical period may or may not indicate a quality problem. Unplanned returns to surgery subject patients to the additional risks inherent in surgical procedures and the inconvenience or unexpected hardships associated with extended length of stay or prolonged recovery periods. Unplanned returns to surgery also add significantly to the cost of treatment.

Calculation Concepts

Numerator=Total Number of Patients Returned to Surgery

Denominator=Total Number of Ambulatory Surgical Patients

Indicator Rate=(Numerator/Denominator)*100

Data Source

Medical Record Abstract Form; Patient Disposition

Indicator 4

Patients admitted to the hospital following surgery

Indicator Logic And Calculation Concepts

Definition

Percent of all patients who were admitted to the hospital as inpatients during the intraoperative or postoperative period.

Type of Indicator

This is a rate-based indicator of total admissions following surgery within the postoperative period addressing a process and outcome of care with an optimal value of zero. This indicator is stated in terms of a negative outcome; therefore, higher rates should be viewed as opportunities for further review and improvement. Lower rates are generally considered better outcomes.

Rationale

Admission to the hospital following ambulatory surgery may or may not indicate a quality problem. Although all patients included in this study were registered and scheduled as ambulatory surgery patients, admissions following surgery may have been anticipated by the physician in advance (e.g., admissions due to the possibility of additional procedures being performed, the condition of the patient, the time for which the procedure was scheduled, etc.). However, unplanned admission subjects a patient to inconvenience or unexpected hardships associated with extended length of sway. Unplanned admissions also add significantly to the cost of treatment.

Calculation Concepts

Numerator=Total Number of Patients Admitted to the Hospital Following Surgery

Denominator=Total Number of Ambulatory Surgical Patients

Indicator Rate=(Numerator/Denominator)*100

Data Source

Medical Record Abstract Form; patient disposition

Indicator 5

Patients expressing pain who did not get relief of pain. (Pain episodes not relieved)

Indicator Logic And Calculation Concepts

Definition

Percent of all patients verbalizing pain during the perioperative period whose pain was not relieved for each of the pain episodes recorded on the Medical Record Abstract Form.

Type of Indicator

This is a rate-based indicator of total patients verbalizing pain during the postoperative period who did not obtain relief of pain addressing a process and outcome of care with an optimal value of zero.

This indicator is stated in terms of a negative outcome; therefore, higher rates should be viewed as opportunities for further review and improvement. Lower rates are generally considered better outcomes.

Rationale

Single or multiple episodes of pain that are unrelieved may or may not indicate a quality problem. Pain episodes, if unrelieved, subject patients to discomfort or other unexpected hardships associated with pain. Severe or unrelieved pain episodes can result in extended length of stay or prolonged recovery periods and may add to patients' dissatisfaction with their treatment.

Calculation Concepts

Numerator=Total Number of Patients Who Were Not Relieved of Pain

Denominator=Total Number of Ambulatory Surgical Patients Who Verbalized Pain

Indicator Rate=(Numerator/Denominator)*100

Data Source

Medical Record Abstract Form; postoperative pain management: A "yes" response to pain verbalized AND a "no" response to pain relieved will be counted as meeting criteria 5, patients expressing pain who did not get relief of pain.

Indicator 6

Patients without significant problems after discharge. (Patients who did not experience any surgically related problems after discharge that required medical intervention)

Indicator Logic And Calculation Concepts

Definition

Percent of all patients interviewed (post-op) who reported none of the following problems:

Nausea
Vomiting
Fever
Difficulty urinating
Bleeding from the site of the procedure
Excessive redness, swelling, or other sign of infection

AND/OR

If one of the above problems was reported, none of the following actions were needed to deal with the problem(s) they experienced:

Visited the physician
Were admitted to the hospital
Received a new or changed prescription
Underwent further surgery
Went to the Emergency Room
Received care from home health care worker Type of Indicator This is a rate-based indicator for patients reporting no significant problems during the postoperative period which required follow-up care with an optimal value of one.

This indicator is stated in terms of a positive outcome; therefore, lower rates should be viewed as opportunities for further review and improvement. Higher rates are generally considered better outcomes.

Rationale

Problems experienced by the patients after discharge related to the surgical procedure may or may not indicate a quality problem. Unexpected problems subject patients to additional risks, inconvenience, or the unexpected hardships associated with prolonged recovery periods. Unexpected problems also add to the cost of treatment.

| Calculation Concepts | |
| --- | --- |
| Numerator = | Total Number of Patients Reporting No Problems Requiring Action After Discharge. |
| Denominator = | Total Number of Ambulatory Surgical Patients Who Participated in the Telephone Interview |
| Indicator Rate = | (Numerator/Denominator) * 100 |

Data Source

Patient Telephone Interview Form:

In order to be counted as meeting this criterion, a "no" response must be present indicating the patient experienced no nausea, vomiting, fever, etc. after leaving the center AND no boxes checked to indicate medical intervention (i.e. called doctor, new prescription, etc.). A "yes" response to any of the post-discharge problems WITH medical intervention will not be counted as meeting this criterion.

Indicator 7

Patients expressing pain after discharge who had relief of pain after utilizing pain control methods as instructed.

Indicator Logic and Calculation Concepts

Definition

Percent of patients interviewed who reported that they were bothered by pain (related to the surgery) after discharge who:

Reported having instructions for using medicines or for using other comfort measures to control pain
AND
Reported that they followed the instructions for using medicines and/or other comfort measures
AND
Reported that the methods that they were instructed to use completely relieved their pain.

Type of Indicator

This is a rate-based indicator of total patients who expressed main after discharge who were relieved of pain using methods prescribed addressing a process and outcome of care with an optimal value of 100%.

This indicator is stated in terms of a positive outcome; therefore, lower rates should be viewed as opportunities for further review and improvement. Higher rates are generally considered better outcomes.

Rationale

Unrelieved post-discharge pain may or may not indicate a quality problem. Such pain, if unrelieved, subjects patients to discomfort or other unexpected hardships associated with pain. Severe or unrelieved pain can result in visits to the physician, ER visits, or prolonged recovery periods, and may add to the dissatisfaction of patients with their treatment.

| Calculation Concepts | |
|---|---|
| Numerator = | Total Number of Patients Completely Relieved of Pain Using Prescribed Methods |
| Denominator = | Total Number of Ambulatory Surgical Patients Reporting Post-Discharge Pain |
| Indicator Rate = | (Numerator/Denominator) * 100 |

Data Source
Patient Telephone Interview Form:
Question 3: A response of "yes" must be present in all subcategories a-d., AND
Question #4 must indicate a score of 1-5 for "completely relieved." Scores of 6-7="greatly relieved;" 8-9="somewhat relieved;" and 10="not relieved." Scores of 6-10 are not considered as meeting this criterion.

Indicator 8

Patients satisfied with pre-operative, intraoperative, and postoperative care.

Indicator Logic and Calculation Concepts

Definition

Percent of patients interviewed who stated that the quality of care that they received during:
The registration and admission process
AND
During the pre-admission testing
AND
During the recovery period in the hospital was excellent.

Type of Indicator

This is a rate-based indicator of total patients rating care as excellent addressing an outcome of care with an optimal value of 100%.

This indicator is stated in terms of a positive outcome; therefore, lower rates should be viewed as opportunities for further review and improvement. Higher rates are generally considered better outcomes.

Rationale

Lower satisfaction levels may or may not indicate a clinical quality problem. However, patients who are satisfied with care are more likely to utilize physician and hospitals services for future care needs. Lower levels of satisfaction will help to flag quality outcomes perceived as problematic from the customer perspective.

| Calculation Concepts | |
|---|---|
| Numerator = | Total Number of Patients Who Rated Care during the Registration and Admission Process, the Pre-admission Testing Period, and the Recovery Period in the Hospital as Excellent |
| Denominator = | Total Number of Ambulatory Surgical Patients Who Participated in the Telephone Interview |
| Indicator Rate = | (Numerator/Denominator) * 100 |

Data Source
Patient Telephone Interview Form:
A response of "excellent" must be present for each of the three processes applicable (i.e. registration/admission, preadmission testing, and recovery). Responses of "fair" and/or "good" are not considered as meeting this criterion. Responses of "N/A" are ignored and are not counted as either meeting or not meeting the criteria. However, if all three responses are "N/A" the case is considered as NOT meeting the criterion of Indicator 8.

Indicator 9

Patients who received and understood discharge instructions.

Indicator Logic and Calculation Concepts

Definition

Percent of patients interviewed who stated that after leaving the hospital they knew:
What problems they might have after surgery
AND
Who to call if they had a problem
AND
What medicines or other methods to use to control pain
AND
When to see their doctor or when to schedule an appointment.

Type of Indicator

This is a rate-based indicator of total patients who received and understood defined aspects of the discharge instructions primarily addressing an outcome of care with an optimal value of 100%.

Rationale

Patients who do not receive or do not understand their discharge instructions may or may not indicate a quality problem at the hospital level. However, understanding of instructions facilitates a smoother recovery and reduces the inconvenience or unexpected hardships associated with inadequate discharge information. Compliance with discharge plans can reduce patient recovery time.

| Calculation Concepts | |
|---|---|
| Numerator = | Total Number of Patients Who Received and Understood Their Discharge Instructions |
| Denominator = | Total Number of Ambulatory Surgical Patients Who Participated in the Telephone Interview |
| Indicator Rate = | (Numerator/Denominator) * 100 |

Data Source
Patient Telephone Interview Form:

A response of "yes" must be present for each of the first four questions asked under question #1 in order to be considered as meeting this criterion. Responses of "somewhat" are not considered as meeting the criteria.

Indicator 10

Patients adequately prepared for self-care at home after discharge.

Indicator Logic and Calculation Concepts
Definition

Percent of patients interviewed who stated that after they were home they felt that they had all of the information that they needed to care for themselves
AND
    that after leaving the hospital they knew
    What problems they might have after surgery
    AND
    Who to call if they had a problem
    AND
    What medicines or other methods to use to control pain
    AND
    When to see their doctor or when to schedule an appointment.

Type of Indicator

This is a rate-based indicator of total patients prepared for care at home after discharge primarily addressing an outcome of care with an optimal value of 100%.

This indicator is stated in terms of a positive outcome; therefore, lower rates should be viewed as opportunities for further review and improvement. Higher rates are generally considered better outcomes.

Rationale

Patients unprepared to care for themselves after discharge may or may not indicate a quality problem. Understanding of self-care instructions facilitates a smoother recovery and reduces the inconvenience or unexpected hardships associated with inadequate discharge information. Compliance with self-care plans can reduce patient recovery time. Lack of preparation for selfcare adds to the cost of care as patients tend to seek care from physicians or hospitals.

| Calculation Concepts | |
| --- | --- |
| Numerator = | Total Number of Patients Prepared for Self-Care after Discharge |
| Denominator = | Total Number of Ambulatory Surgical Patients Who Participated in the Telephone Interview |
| Indicator Rate = | (Numerator/Denominator) * 100 |

Data Source
Patient Telephone Interview Form:

A response of "yes" must be present to the fifth question asked under question #1, AND all of the elements for criterion 9 (i.e. "yes" response to the first four questions) must also be satisfied in order to be considered as meeting criterion 10.

These indicators are exemplary and many can be modified to adjust to changing user needs, new developments in the field and regulatory requirements for example.

For the example given, the first five indicators are displayed as "negative" outcomes (optimal outcome is 0 percent); the last five indicators are displayed as "positive" outcomes with an optimal value of 100 percent.

The present invention is not to be limited in scope by the specific embodiments described herein. Indeed, various modifications of the present invention, in addition to those described herein, will be apparent to those of ordinary skill in the art from the foregoing description and accompanying drawings. Thus, such modifications are intended to fall within the scope of the following appended claims. Further, although the present invention has been described herein in the context of a particular implementation in a particular environment for a particular purpose, those of ordinary skill in the art will recognize that its usefulness is not limited thereto and that the present invention can he beneficially implemented in any number of environments for any number of purposes. Accordingly, the claims set forth below should be construed in view of the full breath and spirit of the present invention as disclosed herein.

What is claimed is:

1. A method for collecting and reporting outcomes data for benchmarking medical procedures comprising the steps of:
    collecting first outcomes data sets for a first plurality of indicators associated with a plurality of medical procedures performed on a first plurality of individuals in a first period of time via a plurality of user interfaces located at a first plurality of user sites, wherein the first plurality of indicators comprise data reflective of the outcome of the plurality of medical procedures performed on the first plurality of individuals from which the first plurality of individuals cannot be identified, and wherein the first plurality of indicators comprises admissions following surgery;
    converting at least some of the first outcomes data sets for the first plurality of indicators associated with one of the plurality of medical procedures into an outcomes data group;
    establishing a norm based at least in part on the outcomes data group;
    collecting second outcomes data sets for a second plurality of indicators associated with one of the plurality of medical procedures performed on a second plurality of individuals in a second period of time via a plurality of user interfaces located at one or more of a second plurality of user sites, wherein the second plurality of indicators comprise data reflective of the outcome of the plurality of medical procedures performed on the second plurality of individuals from which the second plurality of individuals cannot be identified, and wherein the second plurality of indicators comprises admissions following surgery;
    converting at least some of the second outcomes data sets for the second plurality of indicators associated with the one of the plurality of medical procedures into at least one outcomes result;
    selecting one of the at least one outcomes result, wherein the selected outcomes result is based on at least some of the second plurality of indicators associated with the one of the plurality of medical procedures performed on the second plurality of individuals;
    comparing the selected one of the at least one outcomes result to the norm; and
    generating at least one outcomes monitoring report comprising the selected one of the at least one outcomes result and the norm, wherein the outcomes monitoring report comprises medical procedure performance outcomes data from which the first plurality of individuals and the second plurality of individuals cannot be identified and from which the outcome for a particular individual in the second plurality of individuals cannot be determined, wherein the outcomes monitoring report comprises outcomes descriptors organized by outcome per surgical procedure, and wherein the outcomes descriptors comprise:
- a first descriptor indicating a relative performance of the selected at least one outcomes result in comparison to the norm;
- a second descriptor indicating a performance trend of the selected at least one outcomes result over time; and
- a third descriptor indicating a rate of complications within the selected at least one outcomes result based on the second plurality of indicators.

2. The method of claim 1, further comprising the step of: transmitting the first data outcomes sets for the first plurality of indicators and the second outcomes data sets for the second plurality of indicators associated with the one of the plurality of medical procedures to a data processor.

3. The method of claim 1, further comprising the step of: selectively restricting access to the at least one outcomes monitoring report.

4. The method of claim 1, further comprising the step of: posting the at least one outcomes monitoring report to a webpage.

5. The method of claim 1, further comprising the step of: collecting the second outcomes data sets for the second plurality of indicators associated with the one of the plurality of medical procedures from at least one of the one or more of the second plurality of user sites at a plurality of discrete intervals.

6. The method of claim 5, further comprising the step of: generating the at least one outcomes monitoring report from at least two of the plurality of discrete intervals.

7. The method of claim 1, further comprising the steps of: individually identifying and converting the second outcomes data sets for each user site of the second plurality of user sites.

8. The method of claim 7, wherein the at least one outcomes monitoring report includes the at least one outcomes result for a selected user site of the second plurality of user sites and at least one comparison of the norm to the least one outcomes result for the selected user site.

9. At least one processor readable medium for storing a computer program of instructions configured to be readable by at least one processor for instructing the at least one processor to execute a computer process for performing the method as recited in claim 1.

10. The method of claim 1, wherein the first plurality of indicators includes at least one of verbal responses, measured analytical data, and observations of a third-party observer.

11. The method of claim 1, wherein the selected outcomes result is based on at least 30 individuals in the second plurality of individuals.

12. A method for collecting and reporting outcomes data for benchmarking surgical procedures comprising the steps of:
    collecting first primary source surgical procedures outcomes data sets including a plurality of responses to a set of indicators associated with a plurality of surgical procedures performed on a first plurality of patients in a first period of time via a plurality of user interfaces located at a first plurality of surgical centers, wherein the plurality of responses to a set of indicators comprise data reflective of the outcome of the plurality of surgical procedures performed on the first plurality of patients from which the first plurality of patients cannot be identified, and wherein the first primary source surgical procedures outcomes data sets comprise admissions following surgery;
    converting at least some of the first primary source surgical procedures outcomes data sets including the plurality of responses to the set of indicators associated with one of the plurality of surgical procedures into an outcomes data group;
    establishing a norm based at least in part on the outcomes data group;
    collecting second primary source surgical procedures outcomes data sets including a plurality of responses to the set of indicators associated with the plurality of surgical procedures performed on a second plurality of patients in a second period of time via a plurality of user interfaces located at one or more of a second plurality of surgical centers, wherein the plurality of responses to a set of indicators comprise data reflective of the outcome of the plurality of surgical procedures performed on the second plurality of patients from which the second plurality of patients cannot be identified, and wherein the second primary source surgical procedures outcomes data sets comprise admissions following surgery;
    converting at least some of the second primary source surgical procedures outcomes data sets including the plurality of responses to the set of indicators associated with the one of the plurality of surgical procedures into at least one outcomes result;
    selecting one of the at least one outcomes result, wherein the selected outcomes result is based on at least some of the set of indicators associated with the one of the plurality of surgical procedures performed on at least some of the second plurality of patients;
    comparing the selected one of the at least one outcomes result to the norm; and
    generating at least one outcomes monitoring report comprising the selected one of the at least one outcomes result and the norm, wherein the outcomes monitoring report comprises surgical procedure performance outcomes data from which the first plurality of patients and the second plurality of patients cannot be identified and from which the outcome for a particular individual in the second plurality of patients cannot be determined, wherein the outcomes monitoring report comprises outcomes descriptors organized by outcome per surgical procedure, and wherein the outcomes descriptors comprise:
    - a first descriptor indicating a relative performance of the selected at least one outcomes result in comparison to the norm;
    - a second descriptor indicating a performance trend of the selected at least one outcomes result over time; and
    - a third descriptor indicating a rate of complications within the selected at least one outcomes result based on the second primary source surgical procedures outcomes data sets.

13. The method of claim 12, further comprising the step of: transmitting the first and second primary source surgical procedures outcomes data sets including the plurality of responses to the set of indicators associated with the plurality of surgical procedures to a data processor.

14. The method of claim 12, further comprising the step of: selectively restricting access to the at least one outcomes monitoring report.

15. The method of claim 12, further comprising the step of:
posting the at least one outcomes monitoring report to a webpage.

16. The method of claim 12, further comprising the steps of:
individually identifying and converting the second primary source surgical procedures outcomes data sets for each surgical center of the one or more of the second plurality of surgical centers.

17. The method of claim 16, wherein the at least one outcomes monitoring report includes the at least one outcomes result for a selected surgical center of the one or more of the second plurality of surgical centers and at least one comparison of the norm to the selected one of the least one outcomes result for the selected surgical center.

18. At least one processor readable medium for storing a computer program of instructions configured to be readable by at least one processor for instructing the at least one processor to execute a computer process for performing the method as recited in claim 12.

19. The method of claim 12, wherein the set of indicators includes at least one of verbal responses, measured analytical data, and observations of a third-party observer.

20. The method of claim 12, wherein the selected outcomes result is based on at least 30 individuals in the second plurality of patients.

21. An apparatus for collecting and reporting outcomes data for benchmarking medical procedures, the apparatus comprising:
a data collection portion including one or more user interfaces located at a first plurality of user sites, wherein the data collection portion collects first outcomes data sets for a first plurality of indicators associated with a plurality of medical procedures in a first period of time performed on a first plurality of individuals and second outcomes data sets for a second plurality of indicators associated with the plurality of medical procedures in a second period of time performed on a second plurality of individuals, wherein the data collection portion strips out personal identifiers of the first plurality of individuals and of the second plurality of individuals from the first outcomes data sets and from the second outcomes data sets, and wherein the first plurality of indicators comprises admissions following surgery and the second plurality of indicators comprises admissions following surgery;
a data processor portion to receive the first and second outcomes data sets for the first and second plurality of indicators associated with one of the plurality of medical procedures from the data collection portion, wherein the data processor portion comprises:
a first converter portion to convert at least some of the first outcomes data sets for the first plurality of indicators associated with one of the plurality of medical procedures into an outcomes data group;
a norm establishing portion to establish a norm based at least in part on the outcomes data group;
a second converter portion to convert at least some of the second outcomes data sets for the second plurality of indicators associated with the one of the plurality of medical procedures into at least one outcomes result;
a selecting portion to select one of the at least one outcomes result, wherein the selected outcomes result is based on at least some of the second plurality of indicators associated with at least some of the second plurality of individuals;
a comparison portion to compare the selected one of the at least one outcomes result to the norm; and
a report generation portion to generate at least one outcomes monitoring report comprising the selected one of the at least one outcomes result and the norm, wherein the outcomes monitoring report comprises medical procedure performance outcomes data from which the first plurality of individuals and the second plurality of individuals cannot be identified and from which the outcome for a particular individual in the second plurality of individuals cannot be determined, wherein the outcomes monitoring report comprises outcomes descriptors organized by outcome per surgical procedure, and wherein the outcomes descriptors comprise:
a first descriptor indicating a relative performance of the selected at least one outcomes result in comparison to the norm;
a second descriptor indicating a performance trend of the selected at least one outcomes result over time; and
a third descriptor indicating a rate of complications within the selected at least one outcomes result based on the second plurality of indicators.

22. The apparatus of claim 21, further comprising a webpage portion to post the at least one outcomes monitoring report to a webpage.

23. The apparatus of claim 21, further comprising a security portion to selectively restrict access to the at least one outcomes result, the at least one outcomes monitoring report, and the first and second outcomes data sets for the first plurality of indicators and second plurality of indicators associated with the one of the plurality of medical procedures.

24. The apparatus of claim 21, wherein the first and second outcomes data sets for the first and second plurality of indicators associated with the one of the plurality of medical procedures are primary source data sets.

25. The apparatus of claim 21, wherein the first plurality of indicators includes at least one of verbal responses, measured analytical data, and observations of a third-party observer.

26. An article of manufacture for collecting and reporting outcomes data for benchmarking medical procedures, the article of manufacture comprising:
at least one processor readable medium; and
instructions carried on the at least one processor readable medium;
wherein the instructions are configured to be readable from the at least one processor readable medium by at least one processor and thereby cause the at least one processor to operate so as to:
collect first outcomes data sets for a first plurality of indicators associated with a plurality of medical procedures performed on a first plurality of individuals in a first period of time via a plurality of user interfaces located at a first plurality of user sites, wherein the first outcomes data sets comprise data reflective of the outcome of the plurality of medical procedures performed on the first plurality of individuals from which the first plurality of individuals cannot be identified, and wherein the first plurality of indicators comprises admissions following surgery;
convert at least some of the first outcomes data sets for the first plurality of indicators associated with one of the plurality of medical procedures into an outcomes data group;
establish a norm based at least in part on the outcomes data group;

collect second outcomes data sets for a second plurality of indicators associated with the one of the plurality of medical procedures performed on a second plurality of individuals in a second period of time via a plurality of user interfaces located at one or more of a second plurality of user sites, wherein the second outcomes data sets comprise data reflective of the outcome of the plurality of medical procedures performed on the second plurality of individuals from which the second plurality of individuals cannot be identified, and wherein the second plurality of indicators comprises admissions following surgery;

convert at least some of the second outcomes data for the second plurality of indicators associated with the one of the plurality of medical procedures into at least one outcomes result;

select one of the at least one outcomes result, wherein the selected outcomes result is based on at least some of the second plurality of indicators associated with at least some of the second plurality of individuals;

compare the selected one of the at least one outcomes result to the norm; and generate at least one outcomes monitoring report comprising the selected one of the at least one outcomes result and the norm, wherein the outcomes monitoring report comprises medical procedure performance outcomes data from which the first plurality of individuals and the second plurality of individuals cannot be identified and from which the outcome for a particular individual in the second plurality of individuals cannot be determined, wherein the outcomes monitoring report comprises outcomes descriptors organized by outcome per surgical procedure, and wherein the outcomes descriptors comprise:

a first descriptor indicating a relative performance of the selected at least one outcomes result in comparison to the norm;

a second descriptor indicating a performance trend of the selected at least one outcomes result over time; and a third descriptor indicating a rate of complications within the selected at least one outcomes result based on the second plurality of indicators.

27. The article of manufacture of claim 26, wherein the first plurality of indicators includes at least one of verbal responses, measured analytical data, and observations of a third-party observer.

28. At least one non-transitory processor readable storage medium for storing a computer program of instructions configured to be readable by at least one processor for instructing the at least one processor to collect and report outcomes data for benchmarking medical procedures by performing the steps of:

collecting first outcomes data sets for a first plurality of indicators associated with a plurality of medical procedures performed on a first plurality of individuals in a first period of time via a plurality of user interfaces located at a first plurality of user sites, wherein the first outcomes data sets comprise data reflective of the outcome of the plurality of medical procedures performed on the first plurality of individuals from which the first plurality of individuals cannot be identified, and wherein the first plurality of indicators comprises admissions following surgery;

converting at least some of the first outcomes data sets for the first plurality of indicators associated with one of the plurality of medical procedures into an outcomes data group;

establishing a norm based at least in part on the outcomes data group;

collecting second outcomes data sets for a second plurality of indicators associated with the one of the plurality of medical procedures performed on a second plurality of individuals in a second period of time via a plurality of user interfaces located at one or more of a second plurality of user sites, wherein the second outcomes data sets comprise data reflective of the outcome of the plurality of medical procedures performed on the second plurality of individuals from which the second plurality of individuals cannot be identified, and wherein the second plurality of indicators comprises admissions following surgery;

converting at least some of the second outcomes data sets for the second plurality of indicators associated with the one of the plurality of medical procedures into at least one outcomes result;

selecting one of the at least one outcomes result, wherein the selected outcomes result is based on at least some of the second plurality of indicators associated with at least some of the second plurality of individuals;

comparing the selected one of the at least one outcomes result to the norm; and generating at least one outcomes monitoring report comprising the selected one of the at least one outcomes result and the norm, wherein the outcomes monitoring report comprises medical procedure performance outcomes data from which the first plurality of individuals and the second plurality individuals cannot be identified and from which the outcome for a particular individual in the second plurality of individuals cannot be determined, wherein the outcomes monitoring report comprises outcomes descriptors organized by outcome per surgical procedure, and wherein the outcomes descriptors comprise:

a first descriptor indicating a relative performance of the selected at least one outcomes result in comparison to the norm;

a second descriptor indicating a performance trend of the selected at least one outcomes result over time; and a third descriptor indicating a rate of complications within the selected at least one outcomes result based on the second plurality of indicators.

29. The non-transitory processor readable storage medium of claim 28, wherein the first plurality of indicators includes at least one of verbal responses, measured analytical data, and observations of a third-party observer.

* * * * *